(12) United States Patent
Duong et al.

(10) Patent No.: US 11,286,234 B2
(45) Date of Patent: Mar. 29, 2022

(54) PHENYL UREA DERIVATIVES AS N-FORMYL PEPTIDE RECEPTOR MODULATORS

(71) Applicant: Allergan, Inc., Irvine, CA (US)

(72) Inventors: Tien T. Duong, Rancho Santa Margarita, CA (US); Richard L. Beard, Newport Beach, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 562 days.

(21) Appl. No.: 16/093,126

(22) PCT Filed: Mar. 28, 2017

(86) PCT No.: PCT/US2017/024491
§ 371 (c)(1),
(2) Date: Oct. 11, 2018

(87) PCT Pub. No.: WO2017/180323
PCT Pub. Date: Oct. 19, 2017

(65) Prior Publication Data
US 2021/0179550 A1 Jun. 17, 2021

Related U.S. Application Data

(60) Provisional application No. 62/321,447, filed on Apr. 12, 2016.

(51) Int. Cl.
| | | |
|---|---|---|
| C07C 275/30 | (2006.01) | |
| C07C 275/34 | (2006.01) | |
| C07C 309/15 | (2006.01) | |
| C07D 257/04 | (2006.01) | |

(52) U.S. Cl.
CPC .......... *C07C 275/30* (2013.01); *C07C 275/34* (2013.01); *C07C 309/15* (2013.01); *C07D 257/04* (2013.01); *C07C 2601/14* (2017.05); *C07C 2601/16* (2017.05); *C07C 2601/18* (2017.05)

(58) Field of Classification Search
None
See application file for complete search history.

(56) References Cited

U.S. PATENT DOCUMENTS

| | | |
|---|---|---|
| 2013/0109866 A1 | 5/2013 | Beard et al. |
| 2013/0191279 A1 | 7/2013 | Caiman et al. |
| 2013/0274230 A1 | 10/2013 | Beard et al. |
| 2014/0256684 A1 | 9/2014 | Beard et al. |
| 2014/0256685 A1 | 9/2014 | Beard et al. |

FOREIGN PATENT DOCUMENTS

| | | |
|---|---|---|
| WO | 2014138037 A1 | 9/2014 |
| WO | 2014138046 A1 | 9/2014 |
| WO | 2015179707 A1 | 11/2015 |
| WO | 2017023907 A1 | 2/2017 |

OTHER PUBLICATIONS

Registry, Chemical Abstracts Service, Columbus, Ohio, US, (Apr. 10, 2011), Database accession No. 1277545-57-9.
Registry, Chemical Abstracts Service, Columbus, Ohio, US, (Nov. 17, 2016), Database accession No. 2033291-23-3.
Alam, A. et al., Redox signaling regulates commensal-mediated mucosal homeostasis and restitution and requires formyl peptide receptor 1, Mucosal Immunology, May 2014, pp. 645-655, vol. 7, No. 3.
Babbin, B.A., Annexin A1 Regulates Intestinal Mucosal Injury, Inflammation, and Repair, The Journal of Immunology, 2008, pp. 5035-5044, 181.
Brecher, J., Graphical Representation of Stereochemical Configuration, Pure Appl. Chem., 2006, 1897-1970, 78 (10).
Chiang, Nan, et al., The Lipoxin Receptor ALX: Potent Ligand-Specific and Stereoselective Actions in Vivo, Pharmacological Reviews, 2006, 463-487, 58, No. 3.
Cross et al., Rules for the Nomenclature of Organic Chemistry, Pure & Appli. Chem, 1976, 11-30, vol. 45.
Giebeler, Arne et al., Deficiency of Formyl Peptide Receptor 1 and 2 Is Associated with Increased Inflammation and Enhanced Liver Injury after LPS-Stimulation, PLoS One, Jun. 2014, pp. 1-12, vol. 9, Issue 6, e100522.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Leoni, Giovanna, et al., Annexin A1, formyl peptide receptor, and NOX1 orchestrate epithelial repair, The Journal of Clinical Investigation, 2013, 443-54, 123.
Liu, Mingyong et al., Formylpeptide receptors are critical for rapid neutrophil mobilization in host defense against Listeria monocytogens, Scientific Reports, 2012, pp. 1-7, vol. 2, 786.
Liu, Mingyong et al., Formylpeptide Receptors Mediate Rapid Neutrophil Mobilization to Accelerate Wound Healing, PLOS One, 2014, pp. 1-7, vol. 9, Issue 3, e90613.

(Continued)

*Primary Examiner* — Sudhakar Katakam
*Assistant Examiner* — Jennifer C Sawyer
(74) *Attorney, Agent, or Firm* — Jonathan Bass

(57) ABSTRACT

The present invention relates to phenyl urea derivatives useful for the treatment of inflammatory diseases, pharmaceutical compositions containing them and their use as tools or as pharmaceuticals as modulators of the N-formyl peptide receptor (FPR), including FPR1 and FPR2, or as selective agonists of the FPR1 receptor.

Formula I

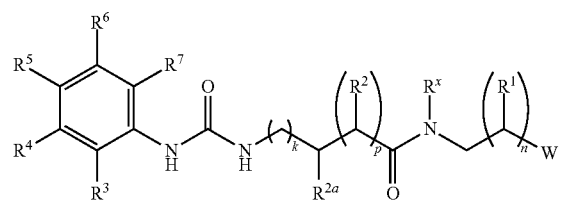

13 Claims, No Drawings

(56) References Cited

OTHER PUBLICATIONS

Oldekamp, Sandra, Lack of formyl peptide receptor 1 and 2 leads to more severe inflammation and higher mortality in mice with of pneumococcal meningitis, Immunology, 2014, pp. 447-461, vol. 143, John Wiley & Sons Ltd.
Perretti, Mauro et al., Therapeutic Anti-Inflammatory Potential of Formyl-Peptide Receptor Agonists, Pharmacology & Research, 2010, 175-188, 127.
Schneider, Erich H., The Leukocyte Chemotactic Receptor FPR1 Is Functionally Expressed on Human Lens Epithelial Cells, The Journal of Biological Chemistry, Nov. 23, 2012, pp. 40779-40792, vol. 287, No. 48.
Tsai, et al., Formyl peptide receptor modulators: a patent review and potential applications for inflammatory: disease, Expert Opinion on Therapeutic Patents, 2016, 1-18, 26 (10).
International Search Report & Written Opinion dated Jul. 31, 2017 for PCT/US2017/024491 filed on Mar. 28, 2017 in the name of Allergan, Inc.

PHENYL UREA DERIVATIVES AS N-FORMYL PEPTIDE RECEPTOR MODULATORS

CROSS-REFERENCE TO RELATED APPLICATIONS

This application is a national stage entry under 35 USC 371 of International Application PCT/US2017/024491, filed Mar. 28, 2017, which claims priority to U.S. Provisional Patent Application No. 62/321,447 filed on Apr. 12, 2016, the entire contents of which are incorporated herein by this specific reference.

FIELD OF THE INVENTION

The present invention relates to phenyl urea derivatives, processes for preparing them, pharmaceutical compositions containing them and their use as pharmaceuticals as modulators of N-formyl peptide receptor(s) (FPR(s)), such as modulators of the N-formyl peptide receptor 1 (FPR1) and the N-formyl peptide receptor 2 (FPR2; also known as FPRL-1 or ALXA4), or as selective modulators of FPR1 relative to FPR2. The invention relates specifically to the use of these compounds and their pharmaceutical compositions to treat disorders associated with FPR modulation, such as FPR1 and FPR2 agonism, FPR1 agonism, or selective agonism of FPR1 relative to FPR2.

BACKGROUND OF THE INVENTION

The FPR family belongs to the seven transmembrane domain chemoattractant G-protein-coupled receptor (GPCR) family. There are three members of this family in humans: FPR1, FPR2 and FPR3. FPRs are critical regulators of host defense in phagocytosis, and are considered highly relevant factors for the chemotaxis of immune cells. These receptors represent an important pro-resolutionary molecular target for the development of new therapeutic agents in diseases or conditions involving excessive inflammatory responses. A review of FPR patent literature was published by Tsai et al. in 2016 (Tsai Y-F, Yang S-C, Hwang T-L, Formyl peptide receptor modulators: a patent review and potential applications for inflammatory disease (2012-2015), *Expert Opinion on Therapeutic Patents*, pp. 1-18, 2016).

FPR2 is expressed predominantly on inflammatory cells, such as monocytes and neutrophils, as well as on T cells, and has been shown to play a critical role in leukocyte trafficking during inflammation and human pathology (See Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. *Pharmacological Reviews* 2006; 58: 463-519).

FPRs are also expressed by immune cells of the central nervous system (CNS), and FPR expression is up-regulated during bacterial meningitis. Lack of FPR1 and FPR2 leads to more severe inflammation and higher mortality in mice infected with *Streptococcus pneumonia* within the CNS, suggesting that these FPRs play an important role in the innate response against this pathogen in the CNS (Oldekamp, S. et al., *Immunology*, 143(3), pp. 447-461, 2014).

FPR1 and FPR2 mediate rapid neutrophil mobilization to accelerate wound healing, as shown in *Listeria*-infected mice. These FPRs sense pathogen-derived chemotactic ligands and recognize host-derived chemotactic peptides in inflammation and injury. The FPRs promote the healing of sterile skin wounds in mice by initiating neutrophil infiltration (Liu, M. et al., *PLoS One*, 9(6): e90613, 2014). FPRs were also shown to guide the first wave of neutrophil infiltration in livers of *Listeria*-infected mice to effectively eliminate the invading pathogen (Liu, M. et al., *Sci. Rep.*, Vol 2, pp. 786, 2012). FPR1 and FPR2 deficiency has been associated with increased inflammation and enhanced liver injury after LPS stimulation. The FPRs appear to play a prominent role in regulating the hepatic inflammatory response after LPS induced liver injury (Giebeler, A. et al., *PLoS One*, 9(6): e100522, 2014).

A complex array of proinflammatory and protective mechanisms regulates inflammation and severity during intestinal mucosal injury. Controlling inflammatory responses and promoting epithelial restitution and barrier recovery requires secretion of anti-inflammatory mediators (Babbin, B. A. et al., *J. Immunol.*, 208, 181(7), pp. 5035-5044). FPR1, a chemo-attractant receptor expressed mainly on leukocytes, is expressed in epithelia, and an FPR1/NADPH oxidase (NOX1)-dependent redox signaling pathway that promotes mucosal wound repair has been delineated in intestinal epithelia. Specific gut microbiota stimulate FPR1 on intestinal epithelial cells, generating reactive oxygen species via enterocyte NOX1, causing rapid phosphorylation of focal adhesion kinase (FAK) and extracellular signal-regulated kinase mitogen-activated protein kinase, which together stimulate migration and proliferation of enterocytes adjacent to colonic wounds. FPR1 was thus identified as a pattern recognition receptor for perceiving the enteric microbiota that promotes mucosal wound repair by generating reactive oxygen species from the enterocyte NOX1. (See Leoni, G. et al., *J. Clin. Invest.*, Vol 123, pp. 443-454, 2013; Alam, A. et al., *Mucosal Immunol.*, 2014, 7(3), pp. 645-655). Regarding FPR2, the role of the ALX/FPR2 receptor-ligand interaction in regulating dextran sulfate sodium (DDS)-induced colitis revealed that treatment with an ALX/FPR2 agonist, 15-epi-lipoxin A4, reverses the enhanced sensitivity of annexin A1 (–/–) mice to DDS-colitis (Babbin, B. A. et al., supra).

FPR1 is also functionally expressed on human lens epithelial cells and appears to have a direct functional role in lens development and maintenance (Schneider et al., *J. Biol. Chem.*, V287, pp. 40779-40792, 2012).

The following are known chemical substances:

CAS Registry No. 1504204-97-0 having the following structure:

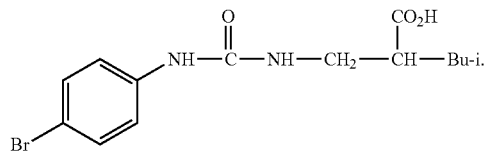

CAS Registry No. 1539675-36-9 having the following structure:

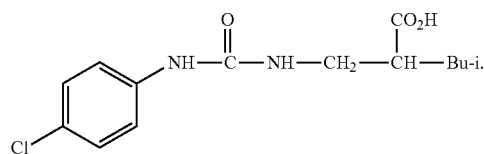

CAS Registry No. 1522199-89-8 having the following structure:

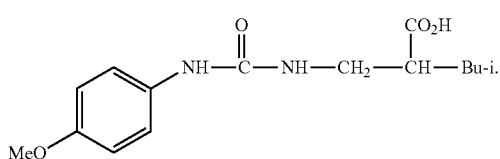

CAS Registry No. 1519281-25-4 having the following structure:

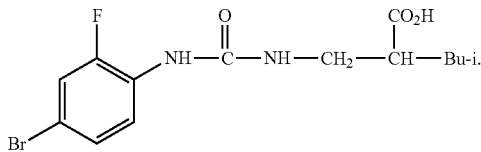

CAS Registry No. 1513978-38-5 having the following structure:

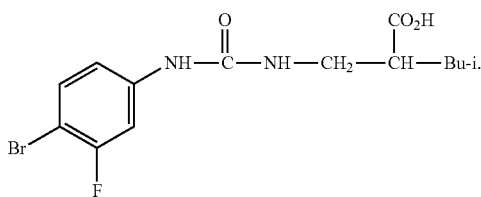

CAS Registry No. 1492252-13-7 having the following structure:

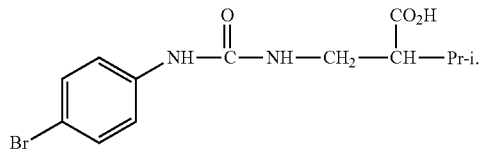

CAS Registry No. 1487893-17-3 having the following structure:

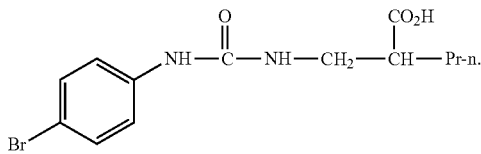

CAS Registry No. 1483767-61-8 having the following structure:

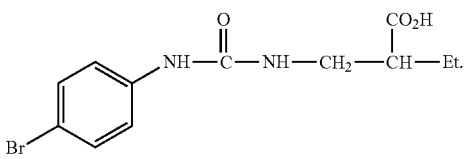 [SMILES: CCC(CNC(=O)Nc1ccc(Br)cc1)C(=O)O]

CAS Registry No. 1284477-37-7 having the following structure:

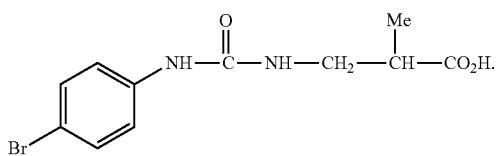 [SMILES: CC(CNC(=O)Nc1ccc(Br)cc1)C(=O)O]

CAS Registry No. 1500296-07-0 having the following structure:

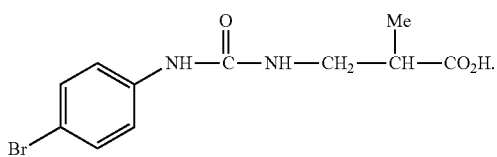 [SMILES: CC(CNC(=O)Nc1ccc(Br)cc1)C(=O)O]

CAS Registry No. 1778230-45-7 having the following structure:

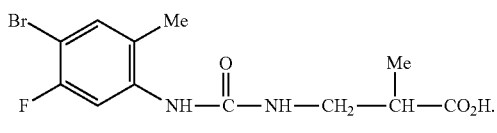

CAS Registry No. 1773390-88-7 having the following structure:

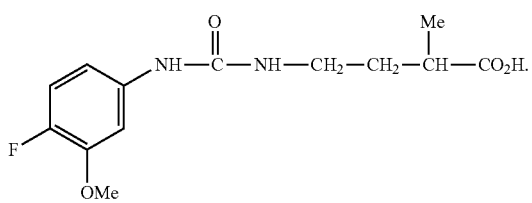 [SMILES: COc1cc(NC(=O)NCCC(C)C(=O)O)ccc1F]

CAS Registry No. 1498807-03-6 having the following structure:

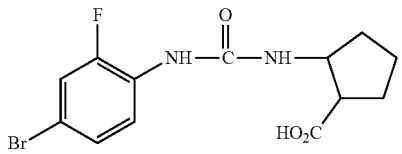 [SMILES: O=C(Nc1ccc(Br)cc1F)NC1CCCC1C(=O)O]

CAS Registry No 1491595-72-2 having the following structure:

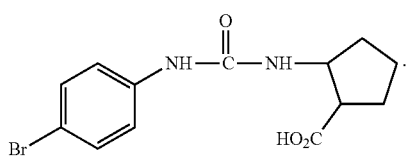 [SMILES: O=C(Nc1ccc(Br)cc1)NC1CCCC1C(=O)O]

CAS Registry No. 1497343-17-5 having the following structure:

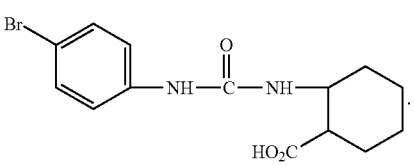 [SMILES: O=C(Nc1ccc(Br)cc1)NC1CCCCC1C(=O)O]

CAS Registry No. 1506132-57-5 having the following structure:

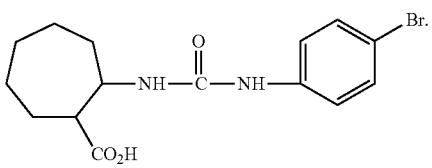 [SMILES: O=C(Nc1ccc(Br)cc1)NC1CCCCCC1C(=O)O]

CAS Registry No. 1376395-61-7 having the following structure:

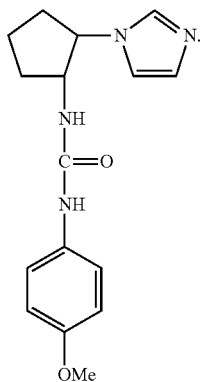 [SMILES: COc1ccc(NC(=O)NC2CCCC2n2ccnc2)cc1]

CAS Registry No. 1797379-98-6 having the following structure:

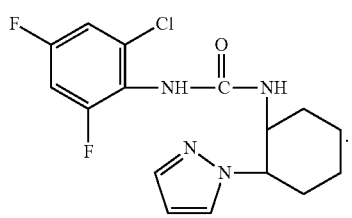 [SMILES: O=C(Nc1c(F)cc(F)cc1Cl)NC1CCCCC1n1cccn1]

US 2013/0109866, the entire disclosure of which is incorporated herein by this specific reference, discloses compounds of the general structure below as FPR modulators for the treatment of a variety of diseases or conditions, including ocular and dermal inflammatory diseases and conditions:

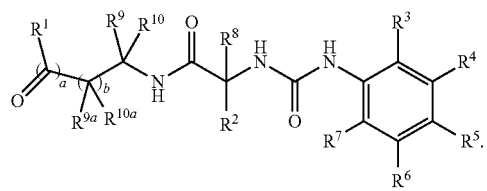

WO2017023907, the entire disclosure of which is incorporated herein by this specific reference, discloses glycine amide compounds of the general structure below, including compounds that exhibit selective agonism of the FPR1 receptor relative to the FPR2 receptor for the treatment of a variety of diseases or conditions, including ocular and dermal inflammatory diseases and conditions:

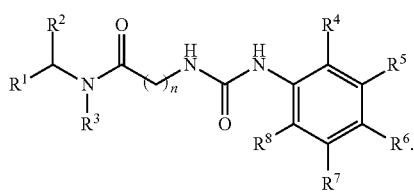

We have discovered new phenyl urea derivatives that exhibit selectivity for FPR1 relative to FPR2.

SUMMARY OF THE INVENTION

A group of phenyl urea derivatives, which are potent FPR modulators and which exhibit selective FPR1 modulation relative to FPR2, has been discovered. As such, the compounds described herein are useful in treating a wide variety of disorders associated with modulation of the FPR receptor, such as modulation of FPR1 and FPR2, or modulation of FPR1, or selective modulation of FPR1 relative to FPR2. The term "modulator" as used herein, includes but is not limited to: receptor agonist, antagonist, inverse agonist, inverse antagonist, partial agonist, and partial antagonist.

This invention describes compounds of Formula I, II and A which modulate FPR biological activity. The compounds in accordance with the present invention are thus of use in medicine, for example, in the treatment of mammalian subjects, including humans, with diseases and/or conditions that are alleviated by FPR modulation, such as FPR1 and FPR2 agonism, or FPR1 agonism, or selective agonism of FPR1 relative to FPR2.

In one aspect, the invention provides a compound of Formula I:

Formula I

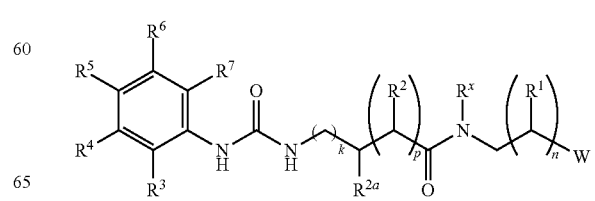

wherein:
W is —COOH, —C(O)OR$^a$, sulfonate, sulfonic acid, phosphonate, phosphonic acid, phosphoric acid, boronic acid or Het$^1$;
wherein R$^a$ is optionally substituted C$_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered heteroaryl optionally substituted with one or more halogen, unsubstituted C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$;
R$^1$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, guanido (—NHC(=NH)NH$_2$), —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^{2a}$ is H, and R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, urea (—NHC(=O)NH$_2$), guanido (—NHC(=NH)NH$_2$), —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle; or
R$^2$ and R$^{2a}$ form an optionally substituted C$_{3-8}$ cycloalkyl or an optionally substituted C$_{3-3}$ cycloalkenyl;
R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^4$ is H, optionally substituted C$_{1-6}$ alkyl, C$_{1-6}$ haloalkyl, halogen, —S(O)$_m$R$^{10}$ or —C(O)R$^{11}$;
R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$;
R$^6$ is H, optionally substituted C$_{1-6}$ alkyl, C$_{1-6}$ haloalkyl, halogen, —S(O)$_m$R$^{10}$ or —C(O)R$^{11}$;
R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{10}$ is —OH, optionally substituted C$_{1-6}$ alkyl or optionally substituted C$_{6-10}$ aryl;
R$^{11}$ is —OH, optionally substituted C$_{1-6}$ alkyl or optionally substituted C$_{6-10}$ aryl;
R$^{12}$ is H or optionally substituted C$_{1-8}$ alkyl;
R$^{13}$ is H, optionally substituted C$_{1-8}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{14}$ is C$_{1-6}$ alkyl;
R$^{15}$ is C$_{1-6}$ alkyl;
R$^{16}$ is C$_{1-6}$ alkyl;
R$^{17}$ is C$_{1-6}$ alkyl;
R$^x$ is H, optionally substituted C$_{1-6}$ alkyl, optionally substituted C$_{6-10}$ aryl or optionally substituted heterocycle;
k is 0, 1 or 2;
each m is independently 1 or 2; and
either n is 0, p is 1 and R$^1$ is absent, or n is 1, p is 0 and R$^2$ is absent;
provided that when p is 0, then R$^{2a}$ is H;
or a mixture of two or more diastereomers thereof;
or a mixture of enantiomers thereof;
or an individual enantiomer or diastereoisomer thereof;
or a pharmaceutically acceptable salt of any one of the foregoing.

In some aspects, the invention provides for a compound of Formula I wherein k is 0 or 1. In other aspects, k is 1. In some aspects, k is 2. Preferably, k is 0.

In another aspect, the invention provides a compound of Formula I for use in a method of treating a disease or condition alleviated by FPR modulation in a subject in need thereof, In another aspect, the invention provides a compound of Formula A for use in treating a disease or condition associated with FPR receptor modulation in a subject in need thereof:

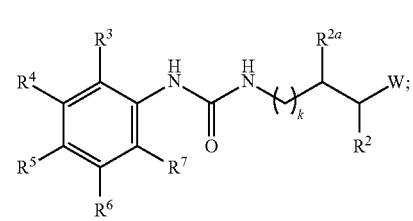

Formula A wherein:
W is —OOH, —C(O)OR$^a$, —C(O)NH$_2$, —C(O)NH(C$_{1-6}$ alkyl), —C(O)N—NR$^{16}$R$^{17}$, sulfonate, sulfonic acid, phosphonate, phosphonic acid, phosphoric acid, boronic acid or Het$^1$;
wherein R$^a$ is optionally substituted C$_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered heteroaryl optionally substituted with one or more halogen, unsubstituted C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$;
R$^{2a}$ is H, and R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, urea (—NHC(=O)NH$_2$), guanido (—NHC(=NH)NH$_2$), —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle; or $R^{2a}$ and $R^2$ form an optionally substituted $C_{3-8}$ cycloalkyl or an optionally substituted $C_{3-8}$ cycloalkenyl;

$R^3$ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —$NR^8R^9$, —$S(O)_mR^{10}$, —$C(O)R^{11}$, —$SR^{12}$ or —$OR^{12}$;

$R^4$ is H, optionally substituted $C_{1-6}$ alkyl, $C_{1-6}$ haloalkyl, halogen, —$S(O)_mR^{10}$ or —$C(O)R^{11}$;

$R^5$ is optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —$S(O)_mR^{10}$, —$C(O)R^{11}$, —$SR^{13}$ or —$OR^{13}$;

$R^6$ is H, optionally substituted $C_{1-6}$ alkyl, $C_{1-6}$ haloalkyl, halogen, —$S(O)_mR^{10}$ or —$C(O)R^{11}$;

$R^7$ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —$NR^8R^9$, —$S(O)_mR^{10}$, —$C(O)R^{11}$, —$SR^{12}$ or —$OR^{12}$;

$R^8$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^9$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^{10}$ is —OH, optionally substituted $C_{1-6}$ alkyl or optionally substituted $C_{6-10}$ aryl;

$R^{11}$ is —OH, optionally substituted $C_{1-6}$ alkyl or optionally substituted $C_{6-10}$ aryl;

$R^{12}$ is H or optionally substituted $C_{1-8}$ alkyl;

$R^{13}$ is H, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^{14}$ is $C_{1-6}$ alkyl;

$R^{15}$ is $C_{1-6}$ alkyl;

$R^{16}$ is $C_{1-6}$ alkyl;

$R^{17}$ is $C_{1-6}$ alkyl;

k is 0, 1 or 2; and each m is independently 1 or 2;

or a mixture of two or more diastereomers thereof;

or a mixture of enantiomers thereof;

or an individual enantiomer or diastereoisomer thereof;

or a pharmaceutically acceptable salt of any one of the foregoing.

In some aspects, the invention provides the compound of Formula A for use in treating the disease or condition associated with FPR receptor modulation in a subject in need thereof, wherein k is 0 or 1. In other aspects, k is 0. In yet other aspects, k is 1. In some aspects, k is 2.

In another aspect, the invention provides a compound of Formula II:

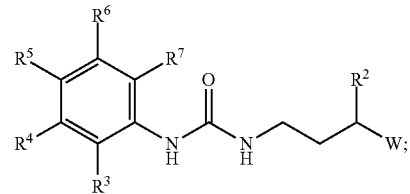

Formula II wherein:

W is —OOH, —$C(O)OR^a$, sulfonate, sulfonic acid, phosphonate, phosphonic acid, phosphoric acid, boronic acid or $Het^1$;

wherein $R^a$ is optionally substituted $C_{1-6}$ alkyl, wherein said optional substituent is selected from the group consisting of —OH, halogen, —$OC_{1-8}$ alkyl and —$(OC_{1-8}$ alkylene$)_q$-$OC_{1-8}$ alkyl, wherein q is 1, 2, 3, 4, 5 or 6; and wherein $Het^1$ is a 5-membered heteroaryl optionally substituted with one or more halogen, unsubstituted $C_{1-6}$ alkyl, —$C_{1-6}$ haloalkyl, —$OC_{1-6}$alkyl, —$(CH_2)_{1-6}OH$, —$(CH_2)_{1-6}NH_2$, —$(CH_2)_{1-6}NH(C_{1-6}$ alkyl$)$ or —$(CH_2)_{1-6}NR^{14}R^{15}$ $R^2$ is (a) unsubstituted $C_{2-6}$ alkyl, (b) —$CH_2$—$(C_{1-5}$ alkyl), wherein said $C_{1-5}$ alkyl is optionally substituted with —OH, —SH, —$OC_{1-6}$ alkyl, —$SC_{1-6}$ alkyl, —$NH_2$, —$NH(C_{1-6}$ alkyl), —$NR^{16}R^{17}$, urea (—NHC(=O)NH_2$), guanido (—NHC(=NH)NH_2$), —COOH, —$C(O)OC_{1-6}$ alkyl, —$C(O)NH_2$, optionally substituted $C_{3-8}$ cycloalkyl, optionally substituted $C_{3-8}$ cycloalkenyl, optionally substituted $C_{6-10}$ aryl or optionally substituted heterocycle, or (c) —$CH_2R^{16}$, wherein $R^{16}$ is an optionally substituted $C_{3-8}$ cycloalkyl, optionally substituted $C_{3-8}$ cycloalkenyl, optionally substituted $C_{6-10}$ aryl or optionally substituted heterocycle;

$R^3$ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —$NR^8R^9$, —$S(O)_mR^{10}$, —$C(O)R^{11}$, —$SR^{12}$ or —$OR^{12}$;

$R^4$ is H, optionally substituted $C_{1-6}$ alkyl, $C_{1-6}$ haloalkyl, halogen, —$S(O)_mR^{10}$ or —$C(O)R^{11}$;

$R^5$ is optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —$S(O)_mR^{10}$, —$C(O)R^{11}$, —$SR^{13}$ or —$OR^{13}$;

$R^6$ is H, optionally substituted $C_{1-6}$ alkyl, $C_{1-6}$ haloalkyl, halogen, —$S(O)_mR^{10}$ or —$C(O)R^{11}$;

$R^7$ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —$NR^8R^9$, —$S(O)_mR^{10}$, —$C(O)R^{11}$, —$SR^{12}$ or —$OR^{12}$;

$R^8$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^9$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^{10}$ is —OH, optionally substituted $C_{1-6}$ alkyl or optionally substituted $C_{6-10}$ aryl;

$R^{11}$ is —OH, optionally substituted $C_{1-6}$ alkyl or optionally substituted $C_{6-10}$ aryl;

$R^{12}$ is H or optionally substituted $C_{1-8}$ alkyl;

$R^{13}$ is H, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle; and $R^{14}$ is $C_{1-6}$ alkyl;

$R^{15}$ is $C_{1-6}$ alkyl;

$R^{16}$ is $C_{1-6}$ alkyl;

$R^{17}$ is $C_{1-6}$ alkyl;

each m is independently 1 or 2;

or a mixture of two or more diastereomers thereof;

or a mixture of enantiomers thereof;

or an individual enantiomer or diastereoisomer thereof;

or a pharmaceutically acceptable salt of any one of the foregoing.

In another aspect of the invention, there are provided pharmaceutical compositions comprising a therapeutically effective amount of at least one compound of the invention described herein in a pharmaceutically acceptable carrier.

In another aspect of the invention, there are provided compounds that selectively agonize FPR1 compared to FPR2, and uses thereof. In further aspects, the compound shows at least 2-fold selectivity for FPR1 compared to FPR2, or at least 5-fold selectivity for FPR1 compared to FPR2. In yet further aspects, the compound shows at least 10-fold selectivity, at least 20-fold selectivity, at least 50-fold selectivity for FPR1 compared to FPR2, at least 100-fold selectivity for FPR1 compared to FPR, at least 150-fold selectivity for FPR1 compared to FPR, or at least 200-fold selectivity for FPR1 compared to FPR2. In the preceding aspects, the selectivity is reported based on the ratio of the $EC_{50}$ for agonizing FPR2 to the $EC_{50}$ for agonizing FPR1.

In yet another aspect of the invention, there are provided methods for treating disorders associated with FPR modulation, such as FPR1 and FPR2 agonism, or FPR1 agonism, or selective agonism of FPR1 relative to FPR2. In other aspects, there are provided uses of compounds of the invention for treating disorders associated with FPR modulation, such as FPR1 and FPR2 agonism, or FPR1 agonism, or selective agonism of FPR1 relative to FPR2. Such methods and uses can be performed, for example, by administering to a subject in need thereof a therapeutically effective amount of at least one compound of the invention, or by administering a pharmaceutical composition containing a therapeutically effective amount of at least one compound of the invention. In some aspects, the disorder is an inflammatory disease or condition. In further aspects, the inflammatory disease or condition is an ocular inflammatory disease or condition, such as dry eye or post-surgical inflammation, including post-cataract surgical inflammation. In yet further aspects, the inflammatory disease or condition is a dermal inflammatory disease or condition, such as psoriasis or rosacea. In further aspects, the subject is a mammal, such as a human or non-human primate.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

The term "alkyl", as used herein, refers to saturated, monovalent hydrocarbon moieties having linear or branched moieties or combinations thereof. Alkyl groups typically contain 1 to 6 carbon atoms (i.e., $C_{1-6}$ alkyl), but may contain a variable number of carbon atoms as specified. For example, an alkyl group may comprise 1 to 4 carbon atoms (i.e., $C_1$ alkyl), or 1 to 3 carbon atoms (i.e., $C_{1-3}$ alkyl). Alkyl groups are optionally substituted with one or more groups including, but not limited to: halogen, hydroxyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid. For example, substituted alkyl includes haloalkyl, such as perhaloalkyl or perfluoroalkyl (e.g., —$CF_3$). In a further example, substituted alkyl includes $C_1$ alkyl substituted with $C_{1-6}$ aryl (e.g., benzyl, which is —$CH_2$-phenyl). One or more methylene ($CH_2$) groups of an alkyl can be replaced by oxygen, sulfur, NH, carbonyl, sulfoxide, sulfonyl, or by a divalent $C_{3-8}$ cycloalkyl; one or more methine (CH) groups of an alkyl can be replaced by nitrogen. Unsubstituted $C_{1-4}$ alkyl includes methyl, ethyl, n-propyl, isopropyl, n-butyl, isobutyl, sec-butyl and t-butyl. Unsubstituted $C_{1-3}$ alkyl includes methyl, ethyl, n-propyl and isopropyl.

The term "alkylene" as used herein refers to a bivalent saturated aliphatic radical derived from an alkene by opening of the double bond, or from an alkane by removal of two hydrogen atoms from different carbon atoms. An alkylene may comprise 1 to 8 carbon atoms (i.e., $C_{1-8}$ alkylene), for example, a $C_1$ alkylene is methylene (—$CH_2$—); a $C_2$ alkylene is ethylene (—$CH_2CH_2$—), and so on.

The term "cycloalkyl", as used herein, refers to a monovalent or divalent group of 3 to 8 carbon atoms (i.e., $C_{3-8}$ cycloalkyl) derived from a saturated cyclic hydrocarbon. Cycloalkyl groups can be monocyclic or polycyclic. Cycloalkyl groups are optionally substituted with one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "cycloalkenyl", as used herein, refers to a monovalent or divalent group of 3 to 8 carbon atoms (i.e., $C_{3-8}$ cycloalkenyl) derived from a saturated cycloalkyl having one or more double bonds. Cycloalkenyl groups can be monocyclic or polycyclic. Cycloalkenyl groups are optionally substituted by one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "heterocycle" as used herein, refers to a 3 to 10 membered ring, which can be aromatic (i.e., a heteroaryl) or non-aromatic, saturated or unsaturated, containing at least one heteroatom selected from the group consisting of O, N and S, and combinations of at least two thereof, interrupting the carbocyclic ring structure. The heterocyclic ring can be interrupted by one or more C=O; the S and/or N heteroatom can be oxidized. Heterocyclic groups can be monocyclic or polycyclic. Heterocyclic ring moieties are optionally substituted with one or more groups including, but not limited to: halogen, hydroxyl, alkyl, —$(CH_2)_{1-6}OH$, —$(CH_2)_{1-6}NH_2$, —$(CH_2)_{1-6}NH(C_{1-6}$ alkyl), —$(CH_2)_{1-6}N(C_{1-6}$ alkyl$)_2$, haloalkyl, cycloalkyl, heterocycle, aryl, ether, amino, alkylamino, nitro, nitrile, amide, sulfonamide, ester, aldehyde, carboxylic acid, ketone, sulfonic acid, phosphonic acid, and/or phosphoric acid.

The term "aryl" as used herein, refers to an aromatic hydrocarbon ring containing 6 to 10 carbon atoms (i.e., $C_{6-10}$ aryl). Aryl groups are optionally substituted by one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid. Aryl can be monocyclic or polycyclic.

The term "halogen", as used herein, refers to an atom of chlorine, bromine, fluorine and/or iodine.

The term "amine" or "amino" as used herein, represents a group of formula "—$NR^xR^y$", wherein $R^x$ and $R^y$ can be the same or independently H, alkyl, aryl, cycloalkyl, cycloalkenyl or heterocycle, as defined above.

The term "amide" as used herein, represents a group of formula "—C(O)N($R^x$)($R^y$)" or "—$NR^x$C(O)$R^y$" wherein $R^x$ and $R^y$ can be the same or independently H, alkyl, aryl, cycloalkyl, cycloalkenyl or heterocycle, as defined above.

The term "sulfonamide" as used herein, represents a group of formula "—S(O)$_2$N($R^x$)($R^y$)" or "—$NR^x$S(O)$_2R^y$" wherein $R^x$ and $R^y$ can be the same or independently H, alkyl, aryl, cycloalkyl, cycloalkenyl or heterocycle, as defined above.

The term "aldehyde" as used herein, represents a group of formula "—C(O)H".

The term "ester" as used herein, represents a group of formula "—C(O)O($R^x$)", wherein $R^x$ is alkyl, aryl, cycloalkyl, cycloalkenyl or heterocycle, as defined above.

The term "ketone" as used herein, represents a group of formula "—C(O)$R^x$" wherein $R^x$ is alkyl, aryl, cycloalkyl, cycloalkenyl or heterocycle, as defined above.

The term "hydroxyl" as used herein, represents a group of formula "—OH".

The term "carbonyl" as used herein, represents a group of formula "—C(O)—".

The term "carboxyl" as used herein, represents a group of formula "—C(O)O—".

The term "carboxylic acid" as used herein, represents a group of formula "—C(O)OH".

The term "carboxylate" as used herein, represents a group of formula "—C(O)O—".

The term "sulfoxide" as used herein, represents a group of formula "—S(O)—".

The term "sulfonyl" as used herein, represents a group of formula "—SO$_2$—".

The term "sulfate" as used herein, represents a group of formula "—OS(O)$_2$O—".

The term "sulphonic acid" as used herein, represents a group of formula "—S(O)$_2$OH".

The term "phosphonic acid" as used herein, represents a group of formula "—P(O)(OH)$_2$".

The term "phosphoric acid" as used herein, represents a group of formula "—(O)P(O)(OH)$_2$".

The term "nitro" as used herein, represents a group of formula "—NO$_2$".

The term "nitrile" as used herein, represents a group of formula "—CN".

The term "ether" as used herein, represents a group of formula "—O$R^x$", wherein R is alkyl, aryl, cycloalkyl, cycloalkenyl or heterocycle, as defined above.

The term "thioether" as used herein, represents a group of formula "—S$R^x$", wherein $R^x$ is alkyl, aryl, cycloalkyl, cycloalkenyl or heterocycle, as defined above.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "carboxylate isostere", as used herein, refers to a moiety that replaces a carboxylic acid, such as a moiety selected from the group consisting of sulfonate, sulfonic acid, phosphonate, phosphonic acid, phosphoric acid, and unsubstituted or substituted 5-membered heteroaryl, preferably tetrazole, imidazole, thiazole, oxazole, triazole, thiophene, pyrazole or pyrole; and wherein said heteroaryl substituent is selected from the group consisting of halogen, —$C_{1-6}$ alkyl, —$C_{1-6}$ haloalkyl, —$OC_{1-6}$alkyl, —$(CH_2)_{1-6}$OH, —$(CH_2)_{1-6}NH_2$, —$(CH_2)_{1-6}NH(C_{1-6}$ alkyl) and —$(CH_2)_{1-6}N(C_{1-6}$ alkyl)$_2$ wherein each $C_{1-6}$ alkyl is the same or different.

The term "therapeutically effective amount" means the amount of a pharmaceutical composition that will elicit a biological or medical response in a subject in need thereof that is being sought by the researcher, veterinarian, medical doctor or other clinician.

The term "pharmaceutically acceptable salts" refers to salts or complexes that retain the desired biological activity of compounds of the invention, and exhibit minimal or no undesired toxicological effects. The "pharmaceutically acceptable salts" according to the invention include therapeutically active, non-toxic base or acid salt forms, which the compounds of Formula I, II or A are able to form. Some compounds of the invention may form salts with acids or bases, including pharmaceutically acceptable acids or bases. Such pharmaceutically acceptable salts of the compounds described herein are within the scope of the invention.

The acid addition salt form of a compound of Formula I, II or A that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic acid and the like. The base addition salt form of a compound of Formula I, II or A that occurs in its acid form can be obtained by treating the acid with an appropriate base such as an inorganic base, for example, sodium hydroxide, magnesium hydroxide, potassium hydroxide, calcium hydroxide, ammonia and the like, or an organic base such as for example, L-arginine, ethanolamine, betaine, benzathine, morpholine and the like. (See Handbook of Pharmaceutical Salts, P. Heinrich Stahl & Camille G. Wermuth (Eds), Verlag Helvetica Chimica Acta, Zürich, 2002, 329-345.)

The compounds of Formula I, II or A and some of their intermediates have at least one asymmetric center in their structure. This assymetric center (or chiral center) may be present in an R or S configuration, said R or S notation is used in correspondence with the rules described in *Pure Appl. Chem.* (1976), 45, 11-13. As such, the compounds of Formula I, II or A may exist in enantiomeric as well as diastereoisomeric forms. It is intended that all stereoisomeric forms of the compounds of Formula I, II or A, as well as mixtures thereof, including racemic mixtures, form part of the present invention. Graphical representation of stereochemical configuration is made in accordance with IUPAC Recommendations (Pure Appl. Chem. (2006), 78(10), pp. 1897-1970). In addition, the present invention embraces all geometric and positional isomers. For example, if a compound of Formula I, II or A incorporates a double bond or a fused ring, both the cis- and trans-forms, as well as mixtures thereof, are embraced within the scope of the invention.

Diastereoisomeric mixtures can be separated into their individual diastereoisomers on the basis of their physicochemical property differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC, or by chiral supercritical fluid chromatography. Also, some of the compounds of the invention may be atropisomers (e.g., substituted biaryls) and are considered as part of this invention.

In particular, a skilled person will realize that even if the absolute stereochemistry of a particular stereoisomer (e.g., an enantiomer or diastereomer) of a molecule is not known, that particular stereoisomer can be distinguished from the other stereoisomers by use of other techniques (e.g., polarimetry, nuclear magnetic resonance spectroscopy, chromatography, and others identifiable to a skilled person). In particular, one exemplary method of distinguishing stereoisomers when the absolute stereochemistry of each stereoisomer is not known is chromatography, such as flash chromatography, medium pressure chromatography, high pressure liquid chromatography (HPLC), and/or supercritical fluid chromatography. In particular, two or more stereoisomers such as diastereomers can be separated and characterized by their retention times, which would be expected to be replicable by using the same chromatographic conditions (e.g., flow rate, column material, solvent systems/gradient profiles, and/or others identifiable to a skilled person). A skilled person will realize that even when the exact absolute or relative retention times of one or more stereoisomers is not replicated (e.g., due to slight variations in the chromatographic parameters and/or chromatographic equipment), a stereoisomer with a shorter retention time can be recognized and said to be "faster eluting,", "earlier eluting" or having a "high Rf," and a stereoisomer with a longer retention time can be recognized and said to be "slower eluting," "later eluting or having a "low Rf." A skilled person will realize that once two or more stereoisomers are distinguished by a technique such as chromatography, the absolute stereochemistry of the stereoisomers can be determined by techniques or combinations of techniques identifiable to a skilled person (e.g., X-ray crystallography, vibrational circular dichroism, nuclear magnetic resonance, total synthesis, and others identifiable to a skilled person).

All stereoisomers (for example, geometric isomers, optical isomers and the like) of the present compounds (including those of the salts and solvates of the compounds, such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The use of the terms "salt", "solvate", and the like, is intended to equally apply to the salt and solvate of enantiomers, stereoisomers, rotamers, tautomers, positional isomers, or racemates of the inventive compounds.

The present invention includes all pharmaceutically acceptable isotopically enriched compounds. Any compound of the invention may contain one or more isotopic atoms enriched or different than the natural ratio, such as deuterium $^2$H (or D) in place of hydrogen $^1$H (or H), or use of $^{13}$C enriched material in place of $^{12}$C and the like. Similar substitutions can be employed for N, O, S and P. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

In an embodiment of the invention, there are provided pharmaceutical compositions including a therapeutically effective amount of at least one compound of the invention in a pharmaceutically acceptable carrier.

The compounds of the invention and the pharmaceutical compositions comprising at least one compound of the invention are indicated for use in treating or preventing conditions in which there is likely to be a component involving the FPR, such as FPR1 and/or FPR2.

In a further embodiment of the invention, there are provided methods for treating disorders associated with FPR modulation (such as FPR1 and FPR2 agonism, or FPR1 agonism, or selective agonism of FPR1 relative to FPR2). Such methods can be performed, for example, by administering to a subject in need thereof a therapeutically effective amount of at least one compound of the invention, or by administering a pharmaceutical composition comprising a therapeutically effective amount of at least one compound of the invention.

More specifically, the present invention provides for:
a compound of the invention for use in the treatment of a mammalian subject (including a human subject) having one or more diseases or conditions that are alleviated by FPR modulation (such as FPR1 and FPR2 agonism, or FPR1 agonism, or selective agonism of FPR1 relative to FPR2); and/or
a method of treating a mammalian subject (including a human subject) having one or more diseases or conditions that are alleviated by FPR modulation (such as FPR1 and FPR2 agonism, or FPR1 agonism, or selective agonism of FPR1 relative to FPR2);
wherein the disease or condition is an ocular inflammatory disease, including but not limited to: age-related macular degeneration, wet macular degeneration, dry macular degeneration, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity, acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, choroiditis, such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, bone marrow transplant retinopathy, corneal wound healing, post-surgical corneal wound healing and/or inflammation, and post-cataract surgical inflammation; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, blepharitis, meibomian gland dysfunction (MDG), glaucoma, branch vein occlusion, Best's vitelliform macular degeneration, retinitis pigmentosa, proliferative vitreoretinopathy (PVR), and any other degenerative disease of either the photoreceptors or the retinal pigment epithelium (Perretti, Mauro et al. Pharmacology & Therapeutics 127 (2010) 175-188).

In other embodiments, the present invention provides for:

a compound of the invention for use in the treatment of a mammalian subject (including a human subject) having one or more diseases or conditions that are alleviated by FPR modulation (such as FPR1 and FPR2 agonism, or FPR1 agonism, or selective agonism of FPR1 relative to FPR2); and/or a method of treating a mammalian subject (including a human subject) having one or more diseases or conditions that are alleviated by FPR modulation (such as FPR1 and FPR2 agonism, or FPR1 agonism, or selective agonism of FPR1 relative to FPR2);

wherein the disease or condition is a dermal inflammatory disease or condition, including, but not limited to: dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

In yet other embodiments, the present invention provides for:

a compound of the invention for use in the treatment of a mammalian subject (including a human subject) having one or more diseases or conditions that are alleviated by FPR modulation (such as FPR1 and FPR2 agonism, or FPR1 agonism, or selective agonism of FPR1 relative to FPR2); and/or a method of treating a mammalian subject (including a human subject) having one or more diseases or conditions that are alleviated by FPR modulation (such as FPR1 and FPR2 agonism, or FPR1 agonism, or selective agonism of FPR1 relative to FPR2);

wherein the disease or condition is: stroke, coronary artery disease, a cardiovascular disorder, coronary artery disease, angina pectoris; or an obstructive airway disease; or a neurological disorder, Alzheimer's disease, neuroinflammation or pain; or an HIV-mediated retroviral infection; or an immunological disorder, arthritis, rheumatoid arthritis, systemic lupus erythematosus, multiple sclerosis; or sepsis; or inflammatory bowel disease (IBD), and/or IBD pain, Crohn's disease or ulcerative colitis; or asthma or an allergic disorder; or cachexia.

In a further embodiment of the invention, the method of treating a disease or condition alleviated by FPR modulation (such as FPR1 and FPR2 agonism, or FPR1 agonism, or selective agonism of FPR1 relative to FPR2), comprises administering to the subject in need of the treatment a therapeutically effective amount of at least one compound of the invention, or an enantiomer, diastereomer or tautomer thereof, or any mixture thereof in any ratio; or a pharmaceutically acceptable salt of any one of the foregoing; thereby treating the disease or condition.

In a further embodiment of the invention, the method of treating a disease or condition alleviated by FPR modulation (such as FPR1 and FPR2 agonism, or FPR1 agonism, or selective agonism of FPR1 relative to FPR2), comprises administering to the subject in need of the treatment a pharmaceutical composition comprising a therapeutically effective amount of at least one compound of the invention, or an enantiomer, diastereomer or tautomer thereof, or any mixture thereof in any ratio; or a pharmaceutically acceptable salt of any one of the foregoing; thereby treating the disease or condition.

In one embodiment, the invention provides for a method of treating a disease or condition in a subject in need of such treatment, the method comprising administering a therapeutically effective amount of a compound of Formula I, II or A, to the subject (or a pharmaceutical composition comprising a therapeutically effective amount of a compound of Formula I, II or A to the subject), thereby treating the disease or condition. In one embodiment, the method comprises administering a compound of Formula I. In another embodiment, the method comprises administering a compound of Formula II. In another embodiment, the method comprises administering a compound of Formula A.

In a further embodiment, the disease or condition is an ocular inflammatory disease or condition. In a further embodiment, the disease or condition is an ocular inflammatory disease or condition selected from the group consisting of: age-related macular degeneration, wet macular degeneration, dry macular degeneration, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity, acute macular neuroretinopathy, central serous chorioretinopathy, cystoid macular edema, and diabetic macular edema; infectious keratitis, herpetic keratitis, corneal angiogenesis, lymphangiogenesis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, bone marrow transplant retinopathy, post-surgical corneal wound healing or inflammation, and post-cataract surgical inflammation; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors, and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, corneal wound healing burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the retinal pigment epithelium. In a further embodiment, the ocular inflammatory disease or condition is selected from the group consisting of: dry eye, a post-surgical corneal wound, post-surgical corneal inflammation, and post-cataract surgical inflammation.

In a further embodiment, there is provided the method of treating the disease or condition associated with FPR modulation, such as FPR1 and FPR2 agonism, or FPR1 agonism, or selective agonism of FPR1 relative to FPR2, wherein the disease or condition is a dermal inflammatory disease or condition. In a further embodiment, the dermal inflammatory disease or condition is selected from the group consisting of: a dermal wound, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms. In a further embodiment, the dermal inflammatory disease or condition is psoriasis or rosacea.

In a further embodiment, there is provided the method of treating the disease or condition associated with FPR modulation, such as FPR1 and FPR2 agonism, or FPR1 agonism, or selective agonism of FPR1 relative to FPR2, wherein the disease or condition is stroke, coronary artery disease, a cardiovascular disorder, coronary artery disease or angina pectoris; or an obstructive airway disease; or a neurological disorder, Alzheimer's disease, neuroinflammation or pain; or an HIV-mediated retroviral infection; or an immunological disorder, arthritis, rheumatoid arthritis, systemic lupus erythematosus, multiple sclerosis; or sepsis; or inflammatory bowel disease or ulcerative colitis; or asthma or an allergic disorder; or cachexia. In one embodiment, the disease or condition is rheumatoid arthritis. In one embodiment, the disease or condition is multiple sclerosis. In another embodiment, the disease or condition is inflammatory bowel disease. In one embodiment, the disease or condition is ulcerative colitis.

In one embodiment, there is provided the method of any one of the preceding embodiments, wherein the subject is a human.

The actual amount of the compound to be administered in any given case will be determined by a physician taking into account the relevant circumstances, such as the severity of the condition, the age and weight of the subject/patient, the patient's general physical condition, the cause of the condition, and the route of administration.

The subject will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains a therapeutically effective amount of one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate, (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose, any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated, the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Preservative-free solutions are often formulated in non-resalable containers containing up to about ten, preferably up to about five units doses, where a typical unit dose is from one to about 8 drops, preferably one to about 3 drops. The volume of one drop usually is about 20-35 microliters.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

In one embodiment, the invention provides for a pharmaceutical composition comprising as active ingredient a therapeutically effective amount of a compound of Formula I, II or A, and a pharmaceutically acceptable carrier. In a further embodiment, there is provided the pharmaceutical composition for use in treating an inflammatory disease or condition in a subject in need of such treatment, wherein the disease or condition is an ocular inflammatory disease or condition, or a dermal inflammatory disease or condition.

Each and every feature described herein, and each and every combination of two or more of such features, is included within the scope of the present invention provided that the features included in such a combination are not mutually inconsistent.

The following are non-limiting embodiments of the invention.

In embodiment (1), there is provided a compound of Formula I:

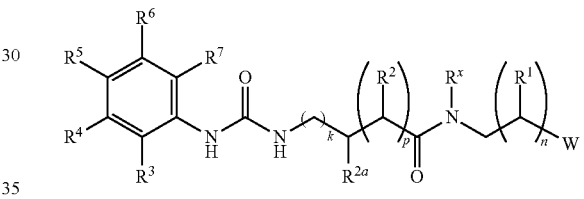

Formula I wherein:
W is —COOH, —C(O)OR$^a$, sulfonate, sulfonic acid, phosphonate, phosphonic acid, phosphoric acid, boronic acid or Het$^1$;
wherein R$^a$ is optionally substituted $C_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered heteroaryl optionally substituted with one or more halogen, unsubstituted $C_{1-6}$ alkyl, —$C_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$;
R$^1$ is optionally substituted $C_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, guanido (—NHC(=NH)NH$_2$), —COOH, —C(O)OC$_{1-6}$ alkyl, —C(O)NH$_2$, optionally substituted $C_{3-8}$ cycloalkyl, optionally substituted $C_{3-8}$ cycloalkenyl, optionally substituted $C_{6-10}$ aryl, and optionally substituted heterocycle;
R$^{2a}$ is H, and R$^2$ is optionally substituted $C_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-8}$ alkyl), —NR$^{16}$R$^{17}$, urea (—NHC(=O)NH$_2$), guanido (—NHC(=NH) NH$_2$), —COOH, —C(O)OC$_{1-8}$ alkyl, —C(O)NH$_2$, optionally substituted $C_{3-8}$ cycloalkyl, optionally substituted $C_{3-8}$ cycloalkenyl, optionally substituted $C_{6-10}$ aryl, and optionally substituted heterocycle; or R² and R²ᵃ form an optionally substituted $C_{3-8}$ cycloalkyl or an optionally substituted $C_{3-8}$ cycloalkenyl;

R³ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —NR⁸R⁹, —S(O)ₘR¹⁰, —C(O)R¹¹, —SR¹² or —OR¹²;

R⁴ is H, optionally substituted $C_{1-6}$ alkyl, $C_{1-6}$ haloalkyl, halogen, —S(O)ₘR¹⁰ or —C(O)R¹;

R⁵ is optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —S(O)ₘR¹⁰, —C(O)R¹¹, —SR¹³ or —OR¹³;

R⁶ is H, optionally substituted $C_{1-6}$ alkyl, $C_{1-6}$ haloalkyl, halogen, —S(O)ₘR¹⁰ or —C(O)R¹;

R⁷ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —NR⁸R⁹, —S(O)ₘR¹⁰, —C(O)R¹¹, —SR¹² or —OR¹;

R⁸ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

R⁹ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

R¹⁰ is —OH, optionally substituted $C_{1-6}$ alkyl or optionally substituted $C_{6-10}$ aryl;

R¹¹ is —OH, optionally substituted $C_{1-6}$ alkyl or optionally substituted $C_{6-10}$ aryl;

R¹² is H or optionally substituted $C_{1-3}$ alkyl;

R¹³ is H, optionally substituted $C_{1-8}$ alkyl, optionally substituted $C_{3-8}$ cycloalkyl, optionally substituted $C_{3-3}$ cycloalkenyl, optionally substituted $C_{6-10}$ aryl or optionally substituted heterocycle;

R¹⁴ is $C_{1-6}$ alkyl;
R¹⁵ is $C_{1-6}$ alkyl;
R¹⁶ is $C_{1-6}$ alkyl;
R¹⁷ is $C_{1-6}$ alkyl;
Rˣ is H, optionally substituted $C_{1-6}$ alkyl, optionally substituted $C_{6-10}$ aryl or optionally substituted heterocycle;

k is 0, 1 or 2;
each m is independently 1 or 2; and
either n is 0, p is 1 and R¹ is absent, or n is 1, p is 0 and R² is absent;
provided that when p is 0, then R²ᵃ is H;
or a mixture of two or more diastereomers thereof;
or a mixture of enantiomers thereof;
or an individual enantiomer or diastereoisomer thereof;
or a pharmaceutically acceptable salt of any one of the foregoing.

In embodiment (2), there is provided the compound of embodiment (1), wherein W is —OOH, sulfonate, sulfonic acid, phosphonate, phosphonic acid, phosphoric acid or Het¹, wherein Het¹ is optionally substituted tetrazole, imidazole, thiazole, oxazole, triazole, isoxazole, oxadiazole, thiadiazole, thiophene, pyrazole or pyrrole; preferably, W is COOH or unsubstituted tetrazole.

In embodiment (3), there is provided the compound of embodiment (1) or (2), wherein k is 0.

In embodiment (4), there is provided the compound of embodiment (1) or (2), wherein k is 1.

In embodiment (5), there is provided the compound of embodiment (1) or (2), wherein n is 0, p is 1, k is 0, and R²ᵃ is H, having the following structure:

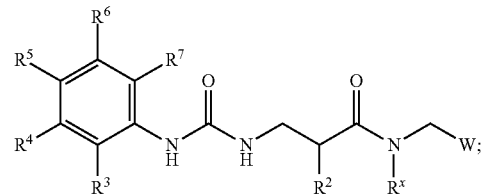

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (6), there is provided the compound of embodiment (1) or (2), wherein n is 0, p is 1, k is 1, and R²ᵃ is H, having the following structure:

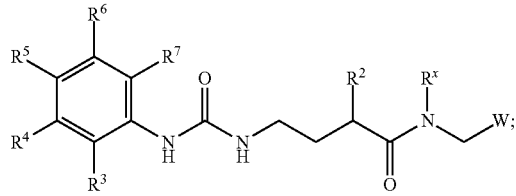

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (7), there is provided the compound of embodiment (1) or (2), wherein n is 1, p is 0, k is 0, and R²ᵃ is H, having the following structure:

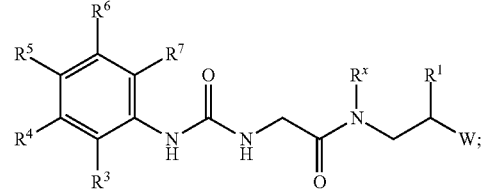

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (8), there is provided the compound of embodiment (1) or (2), wherein n is 1, p is 0, k is 1, and R²ᵃ is H, having the following structure:

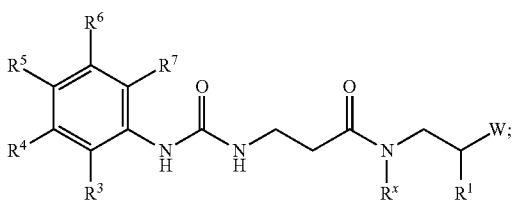

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (9), there is provided the compound of embodiment (1) or (2), wherein n is 0, p is 1, k is 0, and $R^2$ and $R^{2a}$ form a hydrocarbon ring A, wherein A is optionally substituted $C_{3-8}$ cycloalkyl or optionally substituted $C_{3-8}$ cycloalkenyl, the compound having the following structure:

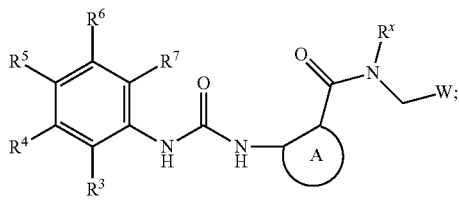

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (10), there is provided the compound of embodiment (1) or (2), wherein n is 0, p is 1, k is 1, and $R^2$ and $R^{2a}$ form a hydrocarbon ring A, wherein A is optionally substituted $C_{3-8}$ cycloalkyl or optionally substituted $C_{3-8}$ cycloalkenyl, the compound having the following structure:

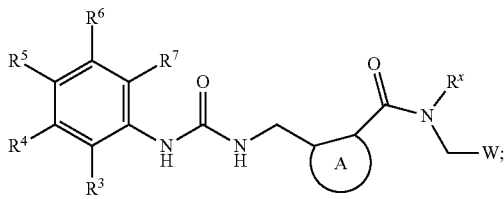

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (11), there is provided the compound of embodiment (9) or (10), wherein A is an optionally substituted $C_{5-8}$ cycloalkyl; preferably, A is an unsubstituted $C_{5-8}$ cycloalkyl.

In embodiment (12), there is provided the compound of any one of embodiments (1) through (4), wherein $R^{2a}$ is H.

In embodiment (13), there is provided the compound of any one of embodiments (1) through (8), wherein n is 1 and $R^1$ is unsubstituted $C_{1-6}$ alkyl, or p is 1 and $R^2$ is unsubstituted $C_{1-6}$ alkyl.

In embodiment (14), there is provided the compound of embodiment (13), wherein $R^1$ or $R^2$ is unsubstituted methyl, ethyl, n-propyl, isopropyl, n-butyl, sec-butyl, isobutyl or tert-butyl; preferably, isobutyl.

In embodiment (15), there is provided the compound of embodiment (14), wherein $R^1$ or $R^2$ has the following structure:

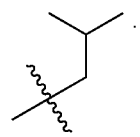 [SMILES: *CC(C)C]

In embodiment (16), there is provided the compound of any one of the preceding embodiments, wherein $R^5$ is $C_{1-6}$ haloalkyl or halogen; or is $C_{1-6}$ haloalkyl, F, Cl or Br; or is $C_{1-6}$ fluoroalkyl or Br; or is $C_{1-6}$ perfluoroalkyl or Br; or is —$CF_3$ or Br; or is —$CF_3$; or is Br.

In embodiment (17), there is provided the compound of any one of embodiments (1) through (8), wherein:
n is 1 and $R^1$ is unsubstituted $C_{1-6}$ alkyl, or p is 1 and $R^2$ is unsubstituted $C_{1-6}$ alkyl;
$R^3$ is H or F;
$R^4$ is H;
$R^5$ is $C_{1-6}$ haloalkyl or halogen;
$R^6$ is H; and
$R^7$ is H or F.

In embodiment (18), there is provided the compound of any one of embodiments (1) through (8), wherein:
n is 1 and $R^1$ is unsubstituted $C_{1-6}$ alkyl, or p is 1 and $R^2$ is unsubstituted $C_{1-6}$ alkyl;
$R^3$ is H;
$R^4$ is H;
$R^5$ is —$CF_3$, fluorine, chlorine or bromine;
$R^6$ is H; and
$R^7$ is H.

In embodiment (19), there is provided the compound of any one of embodiments (1) through (8), wherein:
n is 1 and $R^1$ is unsubstituted n-propyl, isopropyl, n-butyl, sec-butyl, isobutyl or tert-butyl, or p is 1 and $R^2$ is unsubstituted n-propyl, isopropyl, n-butyl, sec-butyl, isobutyl or tert-butyl;
$R^3$ is H;
$R^4$ is H;
$R^5$ is —$CF_3$, chlorine or bromine;
$R^6$ is H; and
$R^7$ is H.

In embodiment (20), there is provided the compound of any one of embodiments (1) through (8), wherein:
n is 1 and $R^1$ is unsubstituted isobutyl, or p is 1 and $R^2$ is unsubstituted isobutyl;
$R^3$ is H;
$R^4$ is H;
$R^5$ is bromine;
$R^6$ is H; and
$R^7$ is H.

In embodiment (21), there is provided the compound of any one of the preceding embodiments, wherein W is —COOH, sulfonate, sulfonic acid, phosphonate, phosphonic acid, phosphoric acid or unsubstituted $Het^1$.

In embodiment (22), there is provided the compound of embodiment (21), wherein W is —COOH, sulfonic acid or tetrazole.

In embodiment (23), there is provided the compound of any one of the preceding embodiments, wherein W is —C(O)OR$^a$; preferably, R$^a$ is unsubstituted C$_{1-6}$ alkyl; optionally, the compound is a prodrug, wherein the ester is hydrolyzed in vivo to provide the corresponding carboxylic acid.

In embodiment (24), there is provided the compound of embodiment (1) or (2), wherein k is 0, R$^{2a}$ is H, R$^x$ is H or methyl, and either n is 1 and R$^1$ is unsubstituted C$_{1-6}$ alkyl, or p is 1 and R$^2$ is C$_{1-6}$ alkyl.

In embodiment (25), there is provided the compound of embodiment (24), wherein n is 1 and R$^1$ is isobutyl, or p is 1 and R$^2$ is isobutyl.

In embodiment (26), there is provided the compound of embodiment (24) or (25), wherein R$^5$ is —CF$_3$ or Br.

In embodiment (27), there is provided the compound of embodiment (25) or (26), wherein each of R$^3$, R$^4$, R$^6$ and R$^7$ is independently selected from H and F, and W is —COOH or tetrazole.

In embodiment (28), there is provided a compound selected from the group consisting of:

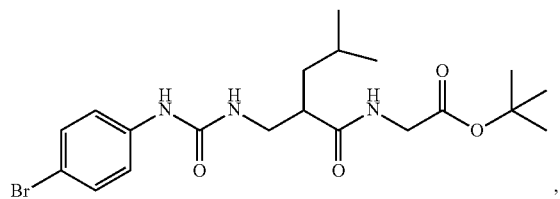

,

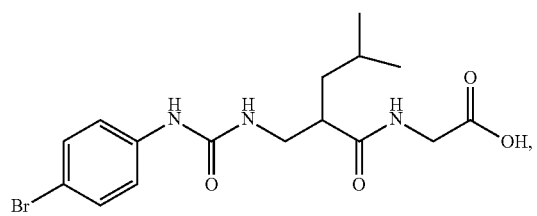

,

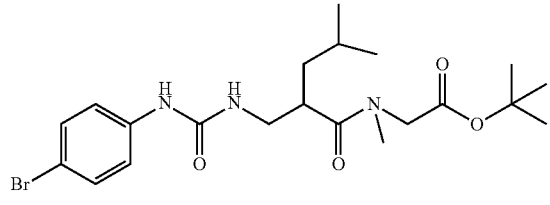

,

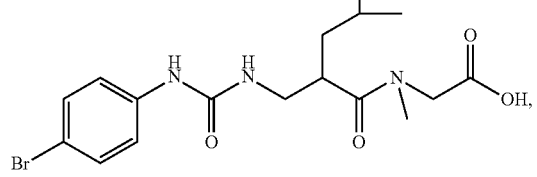

,

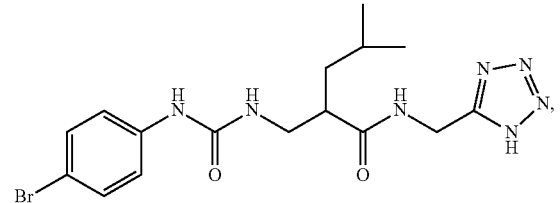

,

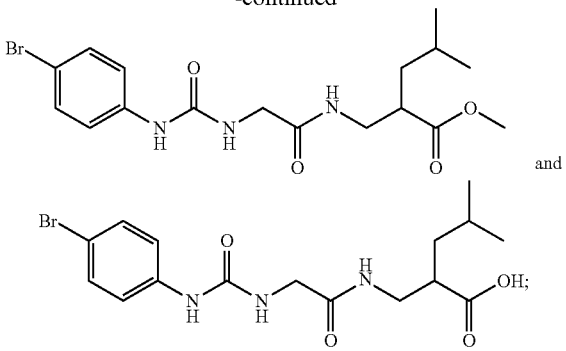

and mixtures of enantiomers thereof;
and individual enantiomers or diastereoisomers thereof;
and pharmaceutically acceptable salts thereof;
preferably, the compound is:

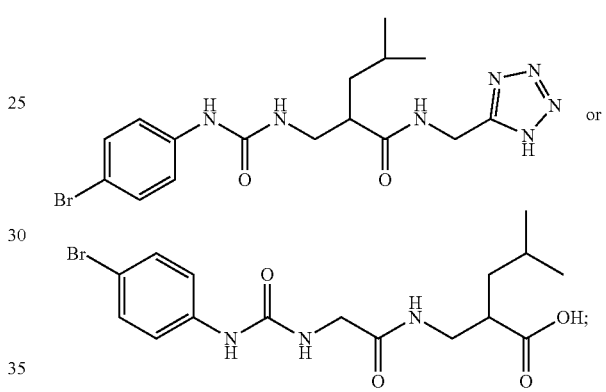

or a mixture of enantiomers of one of the foregoing,
or an individual enantiomer thereof;
or a pharmaceutically acceptable salt thereof.

In embodiment (29), there is provided a pharmaceutical composition comprising a compound of any one of embodiments (1) through (28) and a pharmaceutically acceptable excipient.

In embodiment (30), there is provided a pharmaceutical composition comprising a therapeutically effective amount of a compound of any one of embodiments (1) through (28), or a pharmaceutically acceptable salt thereof, and a pharmaceutically acceptable excipient.

In embodiment (31), there is provided the pharmaceutical composition of embodiment (29) or (30), wherein the pharmaceutically acceptable excipient is an ophthalmically acceptable excipient.

In embodiment (32), there is provided a method of treating a disease or condition associated with FPR modulation in a subject in need thereof, the method comprising administering to the subject (a) a therapeutically effective amount of a compound of any one of embodiments (1) through (28); or (b) a pharmaceutical composition of any one of embodiments (29) through (31), thereby treating the disease or condition.

In embodiment (33), there is provided the method of embodiment (32), wherein the disease or condition is an ocular inflammatory disease or condition, and the method treats the condition.

In embodiment (34), there is provided the method of embodiment (33), wherein the disease or condition is dry eye.

In embodiment (35), there is provided the method of embodiment (33), wherein the disease or condition is suppressed tear production, and the method results in the enhancement of tear production; in a further embodiment, the suppressed tear production is due to ocular inflammation associated with keratoconjunctivitis sicca (dry eye disease).

In embodiment (36), there is provided the method of embodiment (32), wherein the disease or condition is a dermal inflammatory disease or condition, and the method reduces the inflammation.

In embodiment (37), there is provided the method of embodiment (36), wherein the disease or condition is psoriasis or rosacea.

In embodiment (38), there is provided the method of embodiment (32), wherein the disease or condition is a gastrointestinal disease or condition, and the method treats the condition; preferably, the disease or condition is inflammatory bowel disease, Crohn's disease or ulcerative colitis.

In embodiment (39), there is provided the method of embodiment (32) or (33), wherein the compound is administered to the subject topically, orally, systemically or via an implant, such as an ocular implant.

In embodiment (40), there is provided the method of any one of embodiments (32) through (39), wherein the subject is a human.

In embodiment (A1), there is provided a method of treating a disease or condition associated with FPR receptor modulation in a subject in need thereof, the method comprising administering to the subject a compound of Formula A:

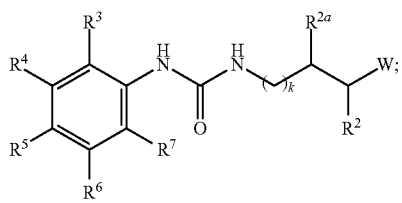

Formula A wherein:
W is —OOH, —C(O)OR$^a$, —C(O)NH$_2$, —C(O)NH(C$_{1-6}$ alkyl), —C(O)N—NR$^{16}$R$^{17}$, sulfonate, sulfonic acid, phosphonate, phosphonic acid, phosphoric acid, boronic acid or Het$^1$;
wherein R$^a$ is optionally substituted C$_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered heteroaryl optionally substituted with one or more halogen, unsubstituted C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH (C$_{1-6}$ alkyl) or —(CH$_2$)$_{1-6}$NR$^{14}$R$^{15}$;
R$^{2a}$ is H, and R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, urea (—NHC(=O)NH$_2$), guanido (—NHC(=NH) NH$_2$), —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle; or
R$^{2a}$ and R$^2$ form an optionally substituted C$_{3-8}$ cycloalkyl or an optionally substituted C$_{3-8}$ cycloalkenyl;

R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^4$ is H, optionally substituted C$_{1-6}$ alkyl, C$_{1-6}$ haloalkyl, halogen, —S(O)$_m$R$^{10}$ or —C(O)R$^{11}$;
R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$;
R$^6$ is H, optionally substituted C$_{1-6}$ alkyl, C$_{1-6}$ haloalkyl, halogen, —S(O)$_m$R$^{10}$ or —C(O)R$^{11}$;
R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^1$;
R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{10}$ is —OH, optionally substituted C$_{1-6}$ alkyl or optionally substituted C$_{6-10}$ aryl;
R$^{11}$ is —OH, optionally substituted C$_{1-6}$ alkyl or optionally substituted C$_{6-10}$ aryl;
R$^{12}$ is H or optionally substituted C$_{1-8}$ alkyl;
R$^{13}$ is H, optionally substituted C$_{1-8}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{14}$ is C$_{1-6}$ alkyl;
R$^{15}$ is C$_{1-6}$ alkyl;
R$^{16}$ is C$_{1-6}$ alkyl;
R$^{17}$ is C$_{1-6}$ alkyl;
k is 0, 1 or 2; and
each m is independently 1 or 2;
or a mixture of two or more diastereomers thereof;
or a mixture of enantiomers thereof;
or an individual enantiomer or diastereoisomer thereof;
or a pharmaceutically acceptable salt of any one of the foregoing.

In embodiment (A2), there is provided the method according to embodiment (A1), wherein the method comprises administering to the subject a therapeutically effective amount of the compound of embodiment (A1), or a pharmaceutical composition comprising a therapeutically effective amount of the compound of embodiment (A1), thereby treating the disease or condition.

In embodiment (A3), there is provided the method according to embodiment (A1) or (A2), wherein W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole; preferably, W is —COOH or —S(O)$_3$H.

In embodiment (A4), there is provided the method according to embodiment (A1), (A2) or (A3), wherein k is 0.

In embodiment (A5), there is provided the method according to embodiment (A1), (A2) or (A3), wherein k is 1.

In embodiment (A6), there is provided the method according to embodiment (A1), (A2) or (A3), wherein k is 0, and $R^{2a}$ is H, and the compound has the following structure:

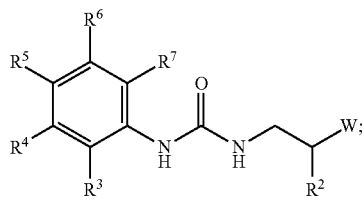

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (A7), there is provided the method according to embodiment (A1), (A2) or (A3), wherein k is 1, and $R^{2a}$ is H, and the compound has the following structure:

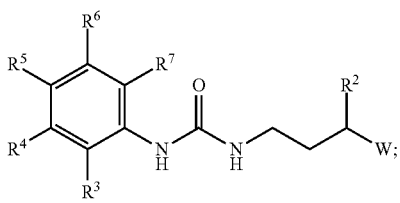

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (A8), there is provided the method according to embodiment (A1), (A2) or (A3), wherein k is 0, and $R^2$ and $R^{2a}$ form a hydrocarbon ring A, wherein A is optionally substituted $C_{3-8}$ cycloalkyl or optionally substituted $C_{3-8}$ cycloalkenyl, and the compound has the following structure:

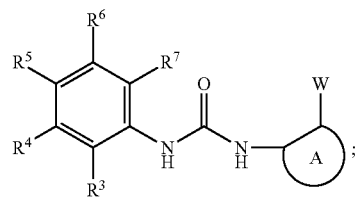

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (A9), there is provided the method according to embodiment (A1), (A2) or (A3), wherein k is 1, and $R^2$ and $R^{2a}$ form a hydrocarbon ring A, wherein A is optionally substituted $C_{3-8}$ cycloalkyl or optionally substituted $C_{3-8}$ cycloalkenyl, and the compound has the following structure:

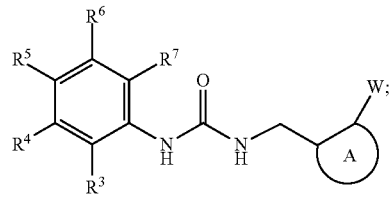

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (A10), there is provided the method according to embodiment (A8) or (A9), wherein A is an optionally substituted $C_{5-8}$ cycloalkyl.

In embodiment (A11), there is provided the method according to embodiment (A10), wherein A is an unsubstituted $C_{5-8}$ cycloalkyl; preferably, A is unsubstituted $C_6$ or $C_8$ cycloalkyl.

In embodiment (A12), there is provided the method according to any one of embodiments (A1) to (A11), wherein $Het^1$ is unsubstituted tetrazole, imidazole, thiazole, oxazole, triazole, isoxazole, oxadiazole, thiadiazole, thiophene, pyrazole or pyrrole.

In embodiment (A13), there is provided the method according to any one of embodiments (A1) through (A7), wherein $R^{2a}$ is H and $R^2$ is unsubstituted $C_{1-6}$ alkyl or benzyl.

In embodiment (A14), there is provided the method according to embodiment (A13), wherein $R^{2a}$ is H and $R^2$ is n-propyl, n-butyl, isobutyl or benzyl.

In embodiment (A15), there is provided the method according to embodiment (A13), wherein $R^{2a}$ is H and $R^2$ has the following structure:

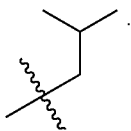 [SMILES: *CC(C)C]

In embodiment (A16), there is provided the method according to any one of the preceding embodiments, wherein $R^5$ is $C_{1-6}$ haloalkyl or halogen; or is $C_{1-6}$ haloalkyl, F, Cl or Br; or is $C_{1-6}$ fluoroalkyl or Br; or is $C_{1-6}$ perfluoroalkyl or Br; or is —$CF_3$ or Br; or is —$CF_3$; or is Br.

In embodiment (A17), there is provided the method according to any one of embodiments (A1) through (A7), wherein:
$R^{2a}$ is H;
$R^2$ is unsubstituted $C_{1-6}$ alkyl or benzyl;
$R^3$ is H or F;
$R^4$ is H;
$R^5$ is $C_{1-6}$ haloalkyl or halogen;
$R^6$ is H; and
$R^7$ is H or F;
preferably, W is not —$C(O)OR^a$.

In embodiment (A18), there is provided the method according to embodiment (A17), wherein $R^3$ is H; $R^5$ is —$CF_3$, fluorine, chlorine or bromine; and $R^7$ is H.

In embodiment (A19), there is provided the method according to embodiment (A17), wherein $R^2$ is unsubstituted n-propyl, isopropyl, n-butyl, sec-butyl, isobutyl, tert-butyl or benzyl; $R^5$ is —$CF_3$, chlorine or bromine; and $R^7$ is H.

In embodiment (A20), there is provided the method according to embodiment (A17), wherein $R^2$ is unsubstituted n-propyl, isobutyl or benzyl.

In embodiment (A21), there is provided the method according to any one of the preceding embodiments, wherein W is —COOH, sulfonate, sulfonic acid, phosphonate, phosphonic acid, phosphoric acid or unsubstituted $Het^1$; wherein $Het^1$ is selected from the group consisting of tetrazole, imidazole, thiazole, oxazole, triazole, isoxazole, oxadiazole, thiadiazole, thiophene, pyrazole or pyrrole, and is preferably tetrazole.

In embodiment (A22), there is provided the method according to any one of the preceding embodiments, wherein W is —COOH or sulfonic acid.

In embodiment (A23), there is provided the method according to embodiment (1), wherein W is —C(O)$OR^a$; optionally, the compound is a prodrug, wherein the ester is hydrolyzed in vivo to provide the corresponding carboxylic acid; preferably:

$R^a$ is unsubstituted $C_{1-6}$ alkyl;

$R^{2a}$ is H;

$R^2$ is unsubstituted $C_{1-6}$ alkyl or benzyl;

$R^3$ is H or F;

$R^4$ is H;

$R^5$ is $C_{1-6}$ haloalkyl or halogen;

$R^6$ is H; and $R^7$ is H or F.

In embodiment (A24), there is provided the method according to embodiment (A1) or (A2), wherein the compound is selected from the group consisting of:

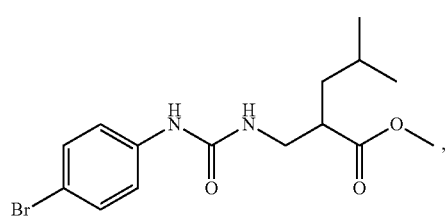

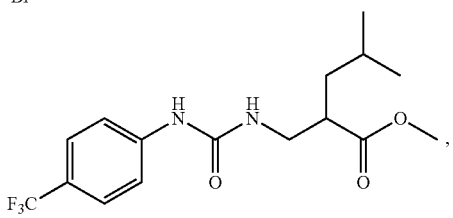

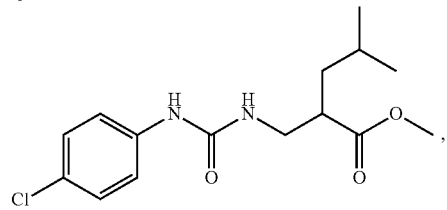

-continued

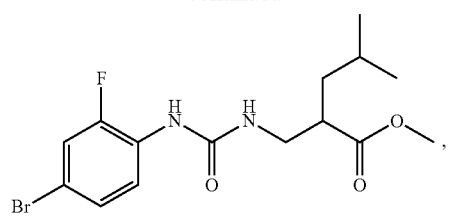

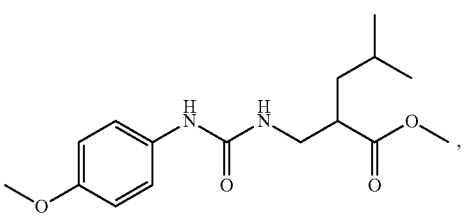

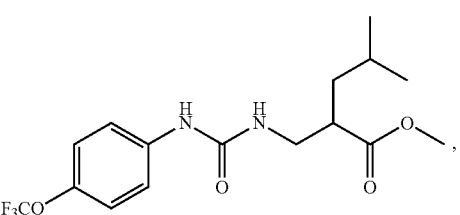

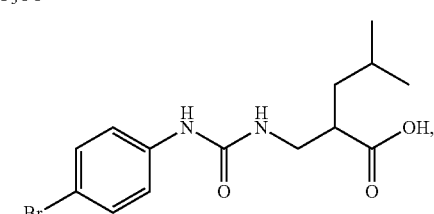

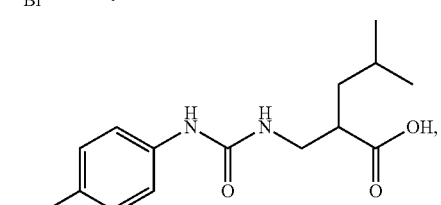

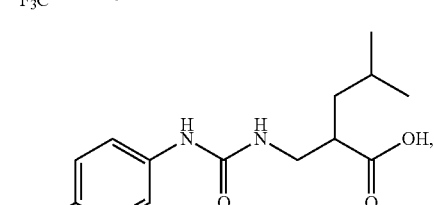

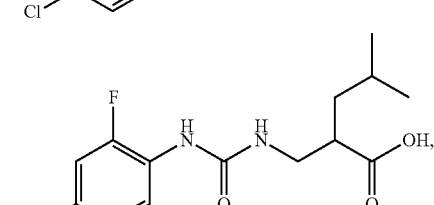

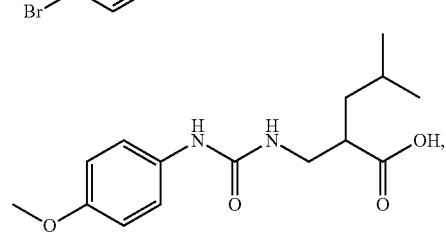

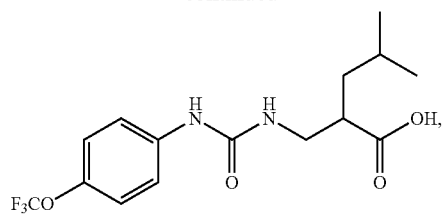
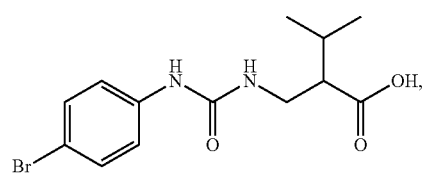
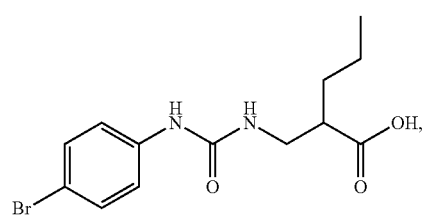
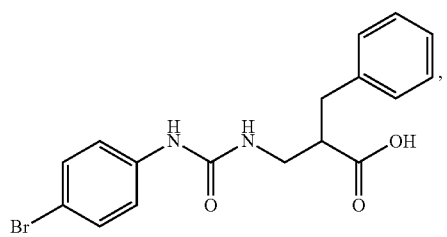
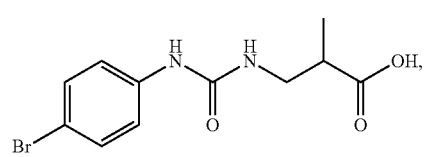
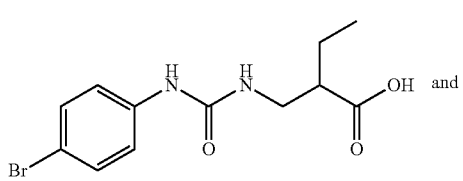
and
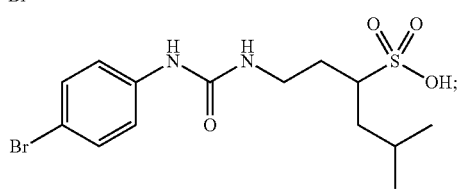
and mixtures of enantiomers thereof;
and individual enantiomers or diastereoisomer thereof;
and pharmaceutically acceptable salts thereof.
In embodiment (A25), there is provided the method according to embodiment (A1) or (A2), wherein the compound is selected from the group consisting of:
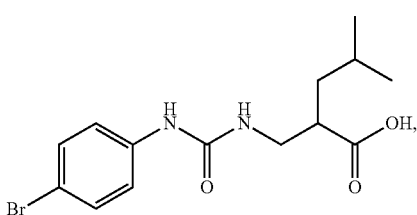
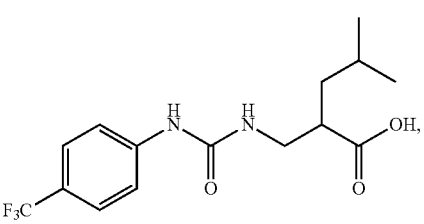
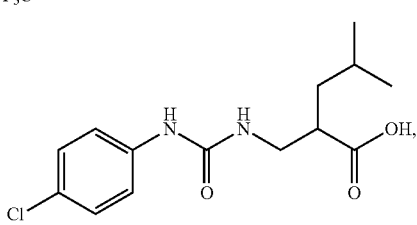
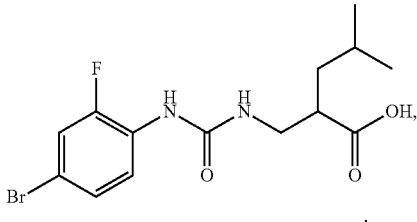
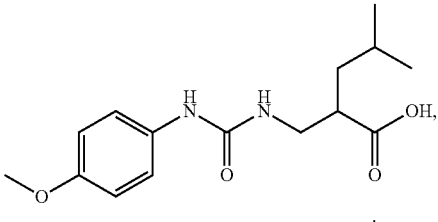
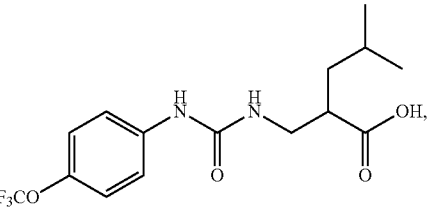
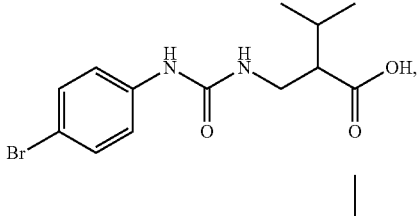
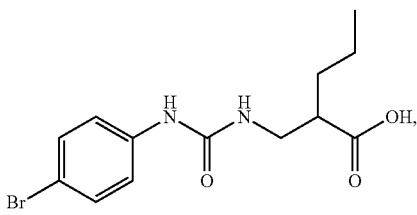

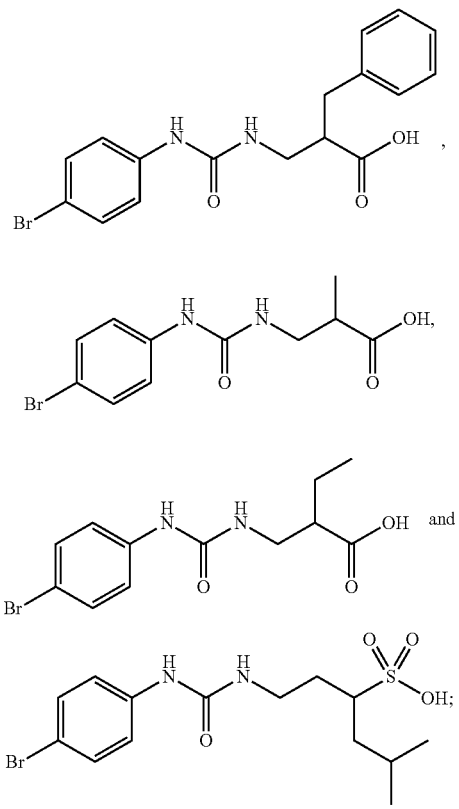

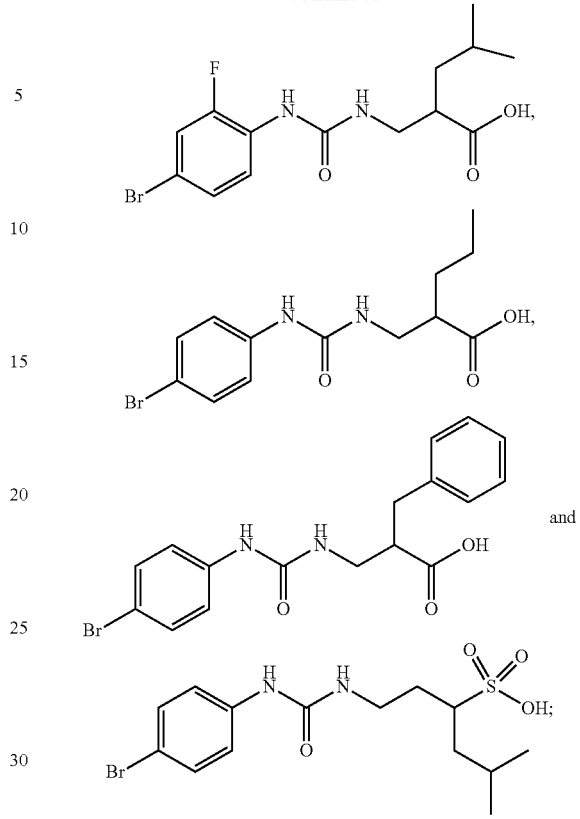

and mixtures of enantiomers thereof;
and individual enantiomers or diastereoisomer thereof;
and pharmaceutically acceptable salts thereof.

In embodiment (A26), there is provided the method according to embodiment (A1) or (A2), wherein the compound is selected from the group consisting of:

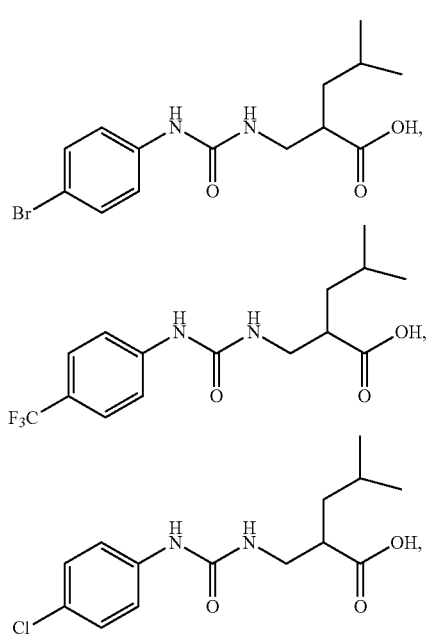

and mixtures of enantiomers thereof;
and individual enantiomers or diastereoisomer thereof;
and pharmaceutically acceptable salts thereof.

In embodiment (A27), there is provided the method according to embodiment (A1), (A2) or (A3), wherein the compound is selected from the group consisting of:

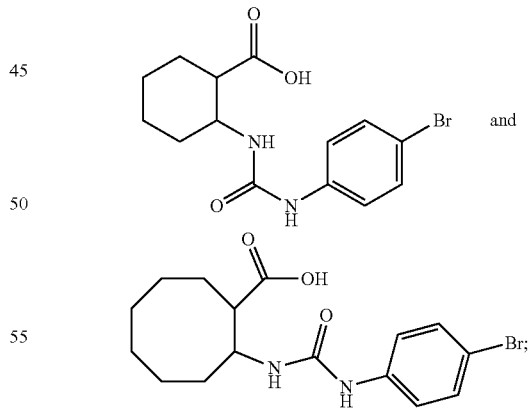

and mixtures of two or more diastereomers thereof;
and mixture of enantiomers thereof;
and individual enantiomers or diastereoisomers thereof;
and pharmaceutically acceptable salts thereof.

In embodiment (A28), there is provided the method according to embodiment (A1) or (A2), wherein the compound is selected from the group consisting of:

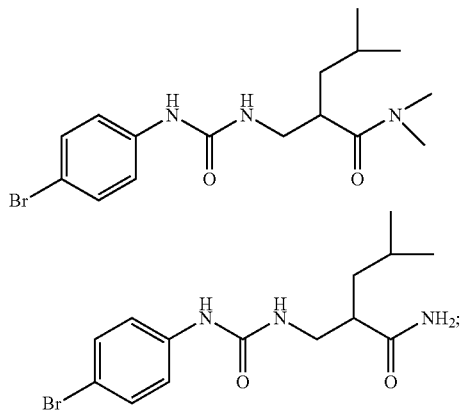

and

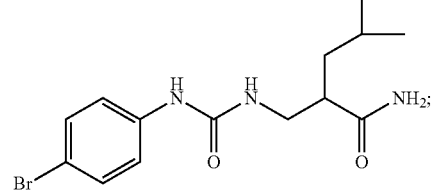

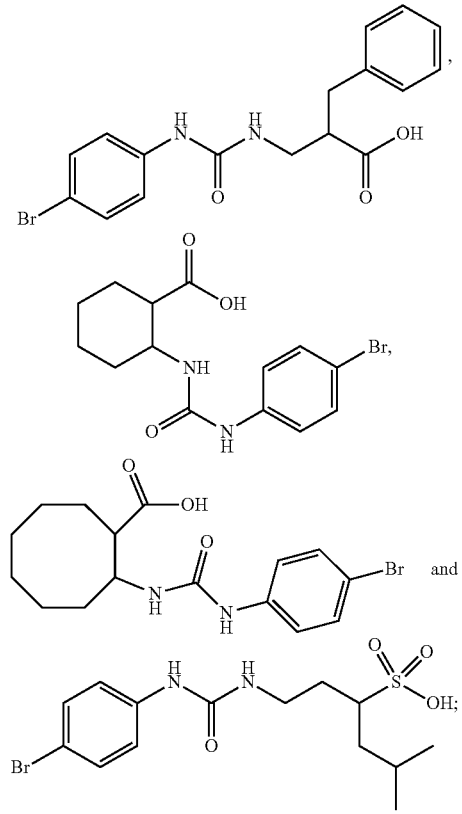

and mixtures of enantiomers thereof;
and individual enantiomers and diastereomers thereof;
and pharmaceutically acceptable salts thereof.

In embodiment (A29), there is provided the method any one of embodiments (A1) through (A28), wherein the disease or condition is an ocular inflammatory disease or condition, and the method treats the condition.

In embodiment (A30), there is provided the method of embodiment (A29), wherein the disease or condition is dry eye.

In embodiment (A31), there is provided the method of embodiment (A29), wherein the disease or condition is suppressed tear production, and the method results in the enhancement of tear production; in a further embodiment, the suppressed tear production is due to ocular inflammation associated with keratoconjunctivitis sicca (dry eye disease).

In embodiment (A32), there is provided the method of any one of embodiments (A1) through (A28), wherein the disease or condition is a dermal inflammatory disease or condition, and the method reduces the inflammation, thereby treating the disease or condition.

In embodiment (A33), there is provided the method of embodiment (A32), wherein the disease or condition is psoriasis or rosacea.

In embodiment (A34), there is provided the method of any one of embodiments (A1) through (A28), wherein the disease or condition is a gastrointestinal disease or condition, and the method treats the condition; preferably, the disease or condition is inflammatory bowel disease, Crohn's disease or ulcerative colitis.

In embodiment (A35), there is provided the method of any one of embodiments (A1) through (A34), wherein the compound is administered to the subject topically, orally, systemically or via an implant, such as an ocular implant.

In embodiment (A36), there is provided the method of any one of embodiments (A1) through (A35), wherein the subject is a human.

In embodiment (A37), there is provided a compound selected from the group consisting of:

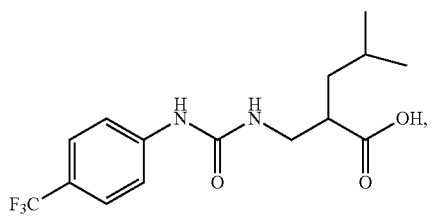

and mixtures of two or more diastereomers thereof;
and mixture of enantiomers thereof;
and individual enantiomers or diastereoisomers thereof;
and pharmaceutically acceptable salts thereof.

In embodiment (A38), there is provided a compound which is:

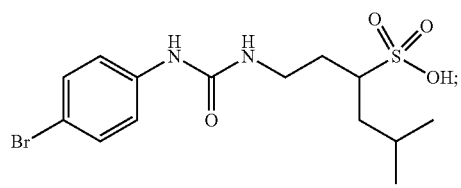 [SMILES: CC(C)CC(CCNC(=O)Nc1ccc(Br)cc1)S(=O)(=O)O]

or a mixture of enantiomers thereof;
or an individual enantiomer thereof;
or a pharmaceutically acceptable salts of any one of the foregoing.

In embodiment (B1), there is provided a compound of Formula II:

Formula II

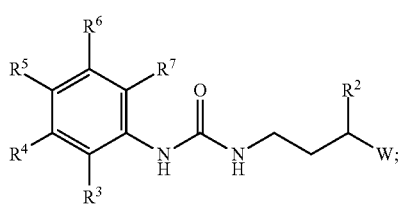

wherein:
W is —OOH, —C(O)OR$^a$, sulfonate, sulfonic acid, phosphonate, phosphonic acid, phosphoric acid, boronic acid or Het$^1$;
wherein R$^a$ is optionally substituted C$_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered heteroaryl optionally substituted with one or more halogen, unsubstituted C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$
R$^2$ is (a) unsubstituted C$_{2-6}$ alkyl, (b) —CH$_2$—(C$_{1-5}$ alkyl), wherein said C$_{1-5}$ alkyl is optionally substituted with —OH, —SH, —OC$_{1-6}$ alkyl, —SC$_{1-6}$ alkyl, —NH$_2$, —NH(C$_{1-6}$ alkyl), —NR$^{16}$R$^{17}$, urea (—NHC(=O)NH$_2$), guanido (—NHC(=NH)NH$_2$), —COOH, —C(O)OC$_{1-6}$ alkyl, —C(O)NH$_2$, optionally substituted C$_{3-8}$ cycloalkyl, optionally substituted C$_{3-3}$ cycloalkenyl, optionally substituted C$_{6-10}$ aryl or optionally substituted heterocycle, or (c) —CH$_2$R$^{16}$, wherein R$^{16}$ is an optionally substituted C$_{3-8}$ cycloalkyl, optionally substituted C$_{3-3}$ cycloalkenyl, optionally substituted C$_{6-10}$ aryl or optionally substituted heterocycle;
R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^4$ is H, optionally substituted C$_{1-6}$ alkyl, C$_{1-6}$ haloalkyl, halogen, —S(O)$_m$R$^{10}$ or —C(O)R$^1$;
R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$;
R$^6$ is H, optionally substituted C$_{1-6}$ alkyl, C$_{1-6}$ haloalkyl, halogen, —S(O)$_m$R$^{10}$ or —C(O)R$^1$;
R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{10}$ is —OH, optionally substituted C$_{1-6}$ alkyl or optionally substituted C$_{6-10}$ aryl;
R$^{11}$ is —OH, optionally substituted C$_{1-6}$ alkyl or optionally substituted C$_{6-10}$ aryl;
R$^{12}$ is H or optionally substituted C$_{1-8}$ alkyl;
R$^{13}$ is H, optionally substituted C$_{1-8}$ alkyl, optionally substituted C$_{3-8}$ cycloalkyl, optionally substituted C$_{3-8}$ cycloalkenyl, optionally substituted C$_{6-10}$ aryl or optionally substituted heterocycle; and
R$^{14}$ is C$_{1-6}$ alkyl;
R$^{15}$ is C$_{1-6}$ alkyl;
R$^{16}$ is C$_{1-6}$ alkyl;
R$^{17}$ is C$_{1-6}$ alkyl;
each m is independently 1 or 2;
or a mixture of two or more diastereomers thereof;
or a mixture of enantiomers thereof;
or an individual enantiomer or diastereoisomer thereof;
or a pharmaceutically acceptable salt of any one of the foregoing.

In embodiment (B2), there is provided the compound of embodiment (B1), wherein W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole; preferably, W is —COOH or sulfonic acid.

In embodiment (B3), there is provided the compound of embodiment (B1) or (B2), wherein R$^2$ is unsubstituted C$_{2-6}$ alkyl.

In embodiment (B4), there is provided the compound of embodiment (B1), (B2) or (B3), wherein R$^2$ is unsubstituted ethyl, n-propyl, isopropyl, n-butyl, sec-butyl, isobutyl or tert-butyl.

In embodiment (B5), there is provided the compound of any one of the preceding embodiments, wherein R$^2$ has the following structure:

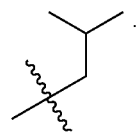 [SMILES: *CC(C)C]

In embodiment (B6), there is provided the compound of embodiment (B1) or (B2), wherein R$^2$ is —CH$_2$—(C$_{1-5}$ alkyl), wherein said C$_{1-5}$ alkyl is optionally substituted with —OH, —SH, —OC$_{1-8}$ alkyl, —SC$_{1-6}$ alkyl, —NH$_2$, —NH(C$_{1-5}$ alkyl), —NR$^{16}$R$^{17}$, urea (—NHC(=O)NH$_2$), guanido (—NHC(=NH)NH$_2$), —COOH, —C(O)OC$_{1-8}$ alkyl or —C(O)NH$_2$; preferably, R$^2$ is unsubstituted —CH$_2$—(C$_{1-5}$ alkyl).

In embodiment (B7), there is provided the compound of (B1) or (B2), wherein R$^2$ is —CH$_2$R$^{16}$, wherein R$^{16}$ is optionally substituted C$_{3-8}$ cycloalkyl, optionally substituted C$_{3-8}$ cycloalkenyl, optionally substituted C$_{6-10}$ aryl or optionally substituted heterocycle; preferably, R$^2$ is benzyl.

In embodiment (B8), there is provided the compound of any one of the preceding embodiments, wherein R$^5$ is C$_{1-6}$ haloalkyl or halogen; or is C$_{1-6}$ haloalkyl, F, Cl or Br; or is C$_{1-6}$ fluoroalkyl or Br; or is C$_{1-6}$ perfluoroalkyl or Br; or is —CF$_3$ or Br; or is —CF$_3$; or is Br.

In embodiment (B9), there is provided the compound of embodiment (B1) or (B2), wherein:
R$^2$ is unsubstituted C$_{2-6}$ alkyl;
R$^3$ is H or F;
R$^4$ is H;
R$^5$ is C$_{1-6}$ haloalkyl or halogen;
R$^6$ is H; and
R$^7$ is H or F.

In embodiment (B10), there is provided the compound of embodiment (B9), wherein:
R$^2$ is unsubstituted C$_{2-6}$ alkyl;
R$^3$ is H;
R$^4$ is H;
R$^5$ is —CF$_3$, fluorine, chlorine or bromine;
R$^6$ is H; and
R$^7$ is H.

In embodiment (B11), there is provided the compound of embodiment (B9), wherein:
$R^2$ is unsubstituted n-propyl, isopropyl, n-butyl, sec-butyl, isobutyl or tert-butyl;
$R^3$ is H;
$R^4$ is H;
$R^5$ is —$CF_3$, chlorine or bromine;
$R^6$ is H; and
$R^7$ is H.

In embodiment (B12), there is provided the compound of embodiment (B9), wherein:
$R^2$ is unsubstituted isobutyl;
$R^3$ is H;
$R^4$ is H;
$R^5$ is bromine;
$R^6$ is H; and
$R^7$ is H.

In embodiment (B13), there is provided the compound of any one of the preceding embodiments, wherein W is —COOH, sulfonate, sulfonic acid, phosphonate, phosphonic acid, phosphoric acid or unsubstituted $Het^1$.

In embodiment (B14), there is provided the compound of any one of the preceding embodiments, wherein W is —COOH, sulfonic acid or tetrazole.

In embodiment (B15), there is provided the compound of any one of the preceding embodiments, wherein W is —COOH or —$SO_3H$.

In embodiment (B16), there is provided the compound of any one of the preceding embodiments, wherein W is —$SO_3H$.

In embodiment (B17), there is provided the compound of embodiment (B1) or (B2), wherein $Het^1$ is an unsubstituted 5-membered heteroaryl; such as an unsubstituted tetrazole, imidazole, thiazole, oxazole, triazole, isoxazole, oxadiazole, thiadiazole, thiophene, pyrazole or pyrrole.

In embodiment (B18), there is provided the compound of embodiment (B1) or (B2), wherein the compound has the following structure:

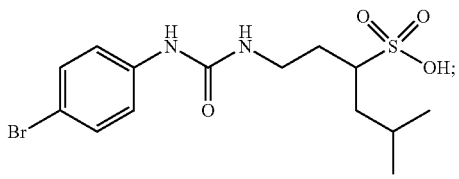

or an individual enantiomer thereof;
or a mixture of enantiomers thereof;
or a pharmaceutically acceptable salt of any one of the foregoing.

In embodiment (B19), there is provided a pharmaceutical composition comprising a compound of any one of embodiments (B1) through (B18) and a pharmaceutically acceptable excipient.

In embodiment (B20), there is provided a pharmaceutical composition comprising a therapeutically effective amount of a compound of any one of embodiments (B1) through (B18), or a pharmaceutically acceptable salt thereof, and a pharmaceutically acceptable excipient.

In embodiment (B21), there is provided the pharmaceutical composition of embodiment (B19) or (B20), wherein the pharmaceutically acceptable excipient is an ophthalmically acceptable excipient.

In embodiment (B22), there is provided a method of treating a disease or condition associated with FPR modulation in a subject in need thereof, the method comprising administering to the subject (a) a therapeutically effective amount of a compound of any one of embodiments (B1) through (B18); or (b) a pharmaceutical composition of any one of embodiments (B19) through (B21), thereby treating the disease or condition.

In embodiment (B23), there is provided the method of embodiment (B22), wherein the disease or condition is an ocular inflammatory disease or condition, and the method treats the condition.

In embodiment (B24), there is provided the method of embodiment (B23), wherein the disease or condition is dry eye.

In embodiment (B25), there is provided the method of embodiment (B23), wherein the disease or condition is suppressed tear production, and the method results in the enhancement of tear production; in a further embodiment, the suppressed tear production is due to ocular inflammation associated with keratoconjunctivitis sicca (dry eye disease).

In embodiment (B26), there is provided the method of embodiment (B22), wherein the disease or condition is a dermal inflammatory disease or condition, and the method reduces the inflammation, thereby treating the disease or condition.

In embodiment (B27), there is provided the method of embodiment (B26), wherein the disease or condition is psoriasis or rosacea.

In embodiment (B28), there is provided the method of embodiment (B22), wherein the disease or condition is a gastrointestinal disease or condition, and the method treats the condition; preferably, the disease or condition is inflammatory bowel disease, Crohn's disease or ulcerative colitis.

In embodiment (B29), there is provided the method of embodiment (B22), wherein the compound is administered to the subject topically, orally, systemically or via an implant, such as an ocular implant.

In embodiment (B30), there is provided the method of any one of embodiments (B22) through (B29), wherein the subject is a human.

In embodiment (C1), there is provided a method of selectively modulating an FPR1 receptor relative to an FPR2 receptor in a recipient, the method comprising administering a compound of Formula I, A or II, or a pharmaceutically acceptable salt thereof, to the recipient, wherein the compound exhibits at least 2-fold selectivity for FPR1 relative to FPR2, and wherein the selectivity is based on the ratio of the $EC_{50}$ for agonizing FPR2 to the $EC_{50}$ for agonizing FPR1 as measured in an in vitro, ex vitro and/or in vivo assay; provided that W is not —$C(O)OR_a$; preferably, the compound is selected from the group consisting of:

(a) a compound of Formula I, wherein:
W is —COOH, sulfonate, sulfonic acid, phosphonate, phosphonic acid, phosphoric acid or $Het^1$, wherein $Het^1$ is optionally substituted tetrazole, imidazole, thiazole, oxazole, triazole, isoxazole, oxadiazole, thiadiazole, thiophene, pyrazole or pyrrole (preferably, W is COOH or unsubstituted tetrazole);
either n is 1, p is 0 and $R^1$ is unsubstituted $C_{1-6}$ alkyl (preferably, isobutyl), or p is 1, n is 0 and $R^2$ is unsubstituted $C_{1-6}$ alkyl (preferably, isobutyl);
$R^{2a}$ is H;
$R^3$ is H or F;
$R^4$ is H;
$R^5$ is $C_{1-6}$ haloalkyl or halogen;
$R^6$ is H;
$R^7$ is H or F;
$R^x$ is H; and
k is 0;

(b) a compound of Formula A, wherein:
W is —COOH, sulfonate, sulfonic acid, phosphonate, phosphonic acid, phosphoric acid or Het¹, wherein Het¹ is optionally substituted tetrazole, imidazole, thiazole, oxazole, triazole, isoxazole, oxadiazole, thiadiazole, thiophene, pyrazole or pyrrole (preferably, W is —COOH or —S(O)₃H);
$R^{2a}$ is H and $R^2$ is unsubstituted $C_{1-6}$ alkyl (preferably, n-propyl or isobutyl) or benzyl; or $R^{2a}$ and $R^2$ form an unsubstituted $C_{3-8}$ cycloalkyl (preferably $C_{5-8}$ or $C_{6-8}$ cycloalkyl);
$R^3$ is H or F;
$R^4$ is H;
$R^5$ is $C_{1-6}$ haloalkyl or halogen;
$R^6$ is H;
$R^7$ is H or F;
$R^x$ is H; and
k is 0 or 1 (preferably, 0); and
(c) a compound of Formula II, wherein
W is —COOH, sulfonate, sulfonic acid, phosphonate, phosphonic acid, phosphoric acid or Het¹, wherein Het¹ is optionally substituted tetrazole, imidazole, thiazole, oxazole, triazole, isoxazole, oxadiazole, thiadiazole, thiophene, pyrazole or pyrrole (preferably, W is —COOH or —S(O)₃H);
$R^2$ is unsubstituted $C_{1-6}$ alkyl (preferably, n-propyl or isobutyl) or benzyl;
$R^3$ is H or F;
$R^4$ is H;
$R^5$ is $C_{1-6}$ haloalkyl or halogen;
$R^6$ is H;
$R^7$ is H or F; and
k is 1;
or a mixture of two or more diastereomers thereof;
or a mixture of enantiomers thereof;
or an individual enantiomer or diastereoisomer thereof,
or a pharmaceutically acceptable salt of any one of the foregoing.

In embodiment (C2), there is provided a method of embodiment (C1), wherein the recipient is a mammalian subject.

In embodiment (C3), there is provided a method of embodiment (C2), wherein the subject is a human.

In embodiment (C4), there is provided a method of embodiment (C1), wherein the recipient is a cell or tissue.

In embodiment (C5), there is provided a method of embodiment (C4), wherein the compound is administered to the cell or tissue recipient in vitro.

In embodiment (C6), there is provided a method of embodiment (C4), wherein the compound is administered to the cell or tissue recipient ex vivo.

In embodiment (C7), there is provided the method of embodiment (C1), wherein the recipient is an in vitro FPR receptor assay system.

In embodiment (C8), there is provided the method of any one of embodiments (C1) through (C7), wherein the compound exhibits at least 5-fold selectivity for FPR1 compared to FPR2.

In embodiment (C9), there is provided the method of any one of embodiments (C1) through (C7), wherein the compound exhibits at least 10-fold selectivity for FPR1 compared to FPR2.

In embodiment (C10), there is provided the method of any one of embodiments (C1) through (C7), wherein the compound exhibits at least 20-fold selectivity for FPR1 compared to FPR2.

In embodiment (C11), there is provided the method of any one of embodiments (C1) through (C7), wherein the compound exhibits at least 50-fold selectivity for FPR1 compared to FPR2.

In embodiment (C12), there is provided the method of any one of embodiments (C1) through (C7), wherein the compound exhibits at least 100-fold selectivity for FPR1 compared to FPR2.

In embodiment (C13), there is provided the method of any one of embodiments (C1) through (C7), wherein the compound exhibits at least 200-fold selectivity for FPR1 compared to FPR2.

In embodiment (C14), there is provided the method of embodiment (C1), wherein the compound is selected from the group consisting of:

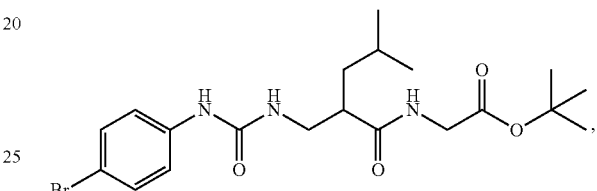

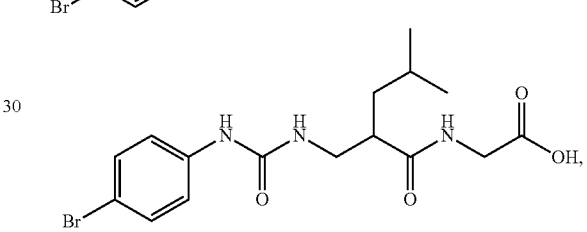

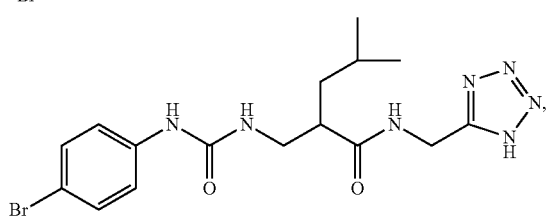

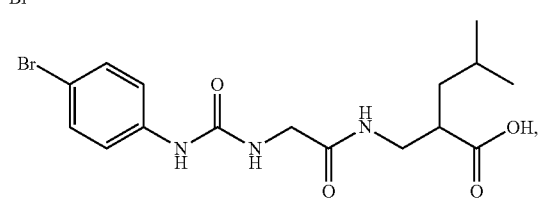

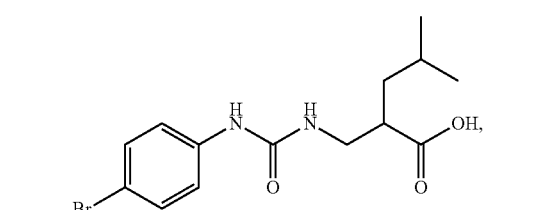

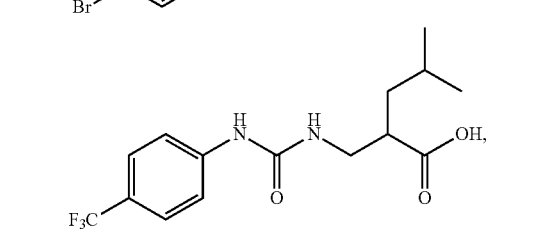

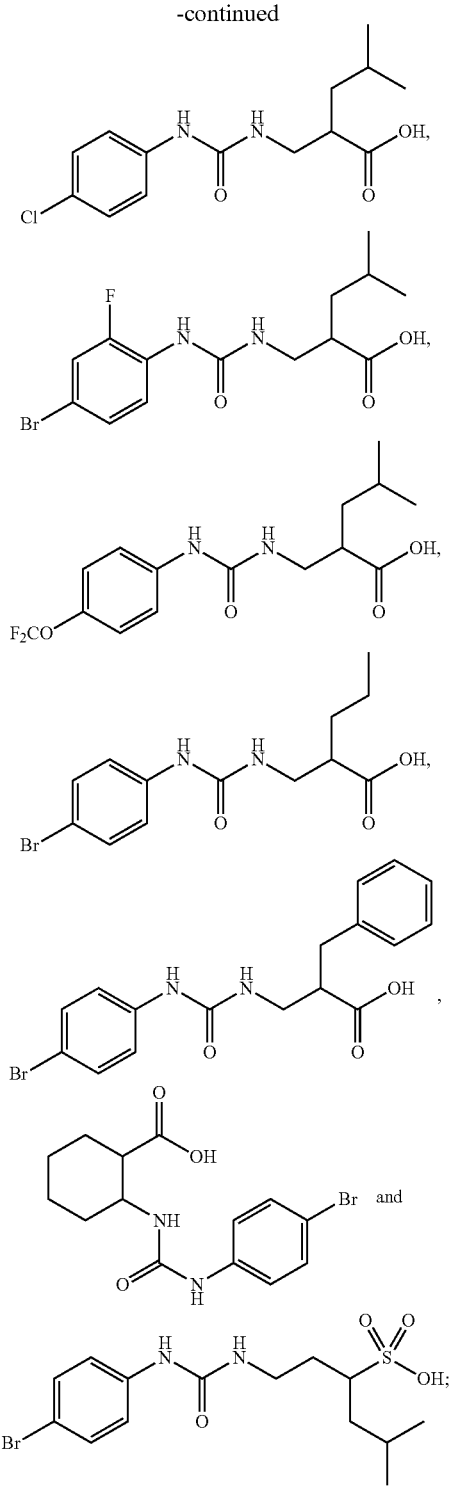
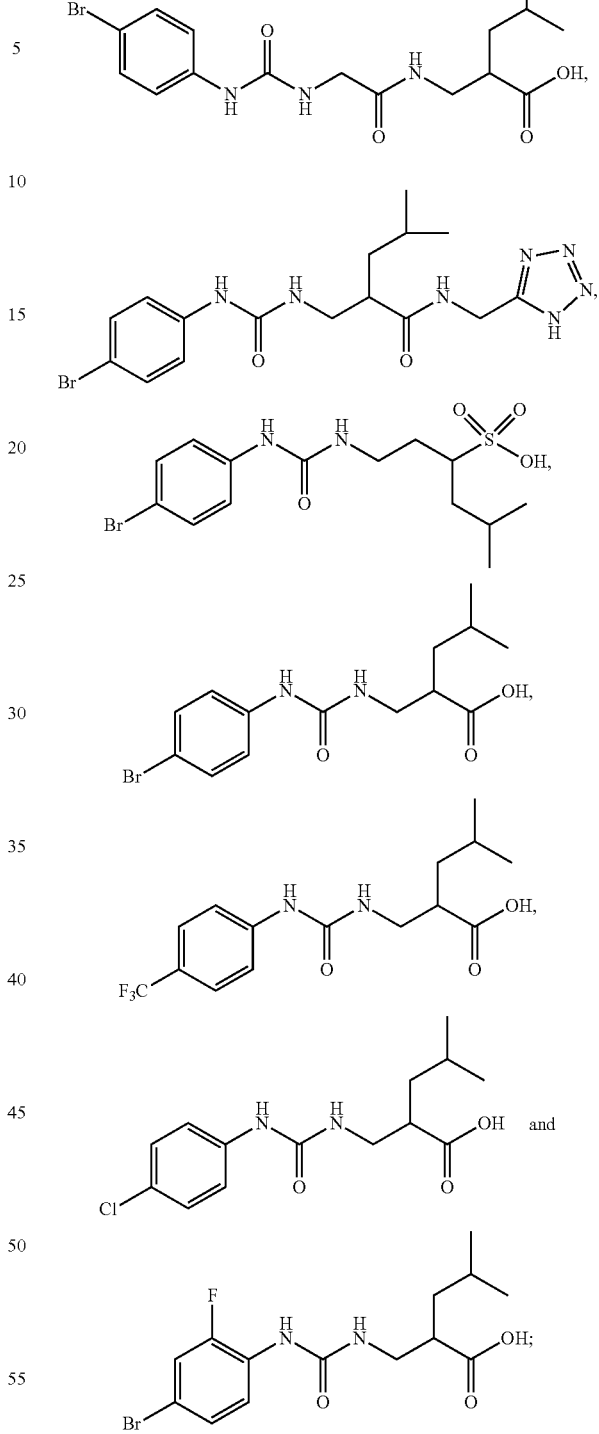

or a mixture of two or more diastereomers thereof;
or a mixture of enantiomers thereof;
or an individual enantiomer or diastereoisomer thereof;
or a pharmaceutically acceptable salt of any of the foregoing.

In embodiment (C15), there is provided the method of embodiment (C1), wherein the compound is selected from the group consisting of:

or a mixture of two or more diastereomers thereof;
or a mixture of enantiomers thereof;
or an individual enantiomer or diastereoisomer thereof;
or a pharmaceutically acceptable salt of any of the foregoing.

In embodiment (C16), there is provided the method of embodiment (C1), wherein the compound is:

(Compound 7)

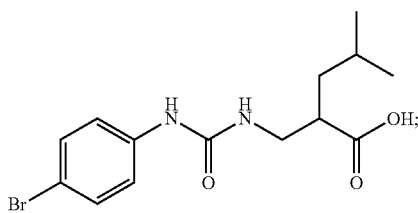

or a mixture of enantiomers thereof;
or an individual enantiomer thereof;
or a pharmaceutically acceptable salt of any one of the foregoing.

In embodiment (C17), there is provided the method of embodiment (C1), wherein the compound is:

(Compound 8)

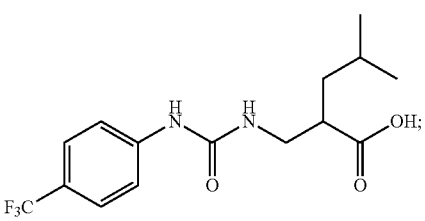

or a mixture of enantiomers thereof;
or an individual enantiomer thereof;
or a pharmaceutically acceptable salt of any one of the foregoing.

In embodiment (C18), there is provided the method of embodiment (C1), wherein the compound is:

(Compound 9)

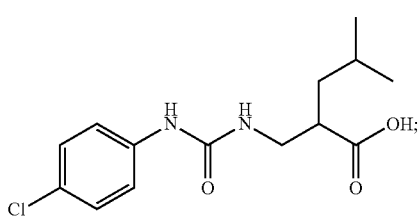

or a mixture of enantiomers thereof;
or an individual enantiomer thereof;
or a pharmaceutically acceptable salt of any one of the foregoing.

In embodiment (C19), there is provided the method of embodiment (C1), wherein the compound is:

(Compound 10)

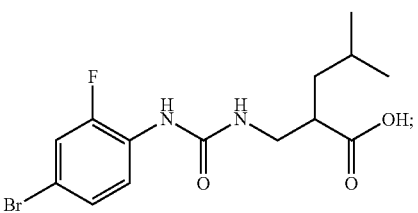

or a mixture of enantiomers thereof;
or an individual enantiomer thereof;
or a pharmaceutically acceptable salt of any one of the foregoing.

In embodiment (C20), there is provided the method of embodiment (C1), wherein the compound is:

(Compound 21)

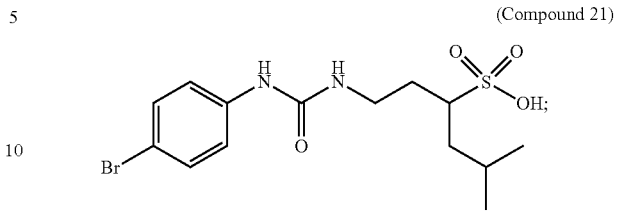

or a mixture of enantiomers thereof;
or an individual enantiomer thereof;
or a pharmaceutically acceptable salt of any one of the foregoing.

In embodiment (C21), there is provided the method of embodiment (C1), wherein the compound is:

(Compound 33)

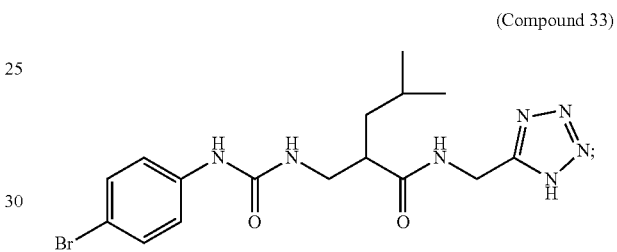

or a mixture of enantiomers thereof;
or an individual enantiomer thereof;
or a pharmaceutically acceptable salt of any one of the foregoing.

In embodiment (C21), there is provided the method of embodiment (C1), wherein the compound is:

(Compound 39)

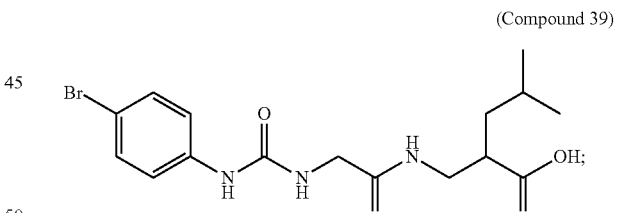

or a mixture of enantiomers thereof;
or an individual enantiomer thereof;
or a pharmaceutically acceptable salt of any one of the foregoing.

In embodiment (D1), there is provided a method of screening for a substance that modulates an FPR receptor, the method comprising:

a) contacting an FPR receptor with a test substance, b) determining the ability of the test substance to modulate the FPR receptor, and c) comparing the ability of the test substance to modulate the FPR receptor with the ability of a compound of Formula I, A or II, or a pharmaceutically acceptable salt thereof, to modulate an FPR receptor of the same subtype(s); provided that W is not —C(O)OR$_a$; preferably, the compound is selected from the group consisting of:
(a) the compound of Formula I, wherein:
W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole (preferably, W is COOH or unsubstituted tetrazole);
either n is 1, p is 0 and R$^1$ is unsubstituted C$_{1-6}$ alkyl (preferably, isobutyl), or p is 1, n is 0 and R$^2$ is unsubstituted C$_{1-6}$ alkyl (preferably, isobutyl);
R$^{2a}$ is H;
R$^3$ is H or F;
R$^4$ is H;
R$^5$ is C$_{1-6}$ haloalkyl or halogen;
R$^6$ is H;
R$^7$ is H or F;
R$^x$ is H; and
k is 0;
(b) the compound of Formula A, wherein:
W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole (preferably, W is —COOH or —S(O)$_3$H);
R$^{2a}$ is H and R$^2$ is unsubstituted C$_{1-6}$ alkyl (preferably, n-propyl or isobutyl) or benzyl; or R$^{2a}$ and R$^2$ form an unsubstituted C$_{3-8}$ cycloalkyl (preferably C$_{5-8}$ or C$_{6-8}$ cycloalkyl);
R$^3$ is H or F;
R$^4$ is H;
R$^5$ is C$_{1-6}$ haloalkyl or halogen;
R$^6$ is H;
R$^7$ is H or F;
R is H; and
k is 0 or 1 (preferably, 0); and
(c) the compound of Formula II, wherein
W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole (preferably, W is —COOH or —S(O)$_3$H);
R$^2$ is unsubstituted C$_{1-6}$ alkyl (preferably, n-propyl or isobutyl) or benzyl;
R$^3$ is H or F;
R$^4$ is H;
R$^5$ is C$_{1-6}$ haloalkyl or halogen;
R$^6$ is H;
R$^7$ is H or F; and
k is 1;
or a mixture of two or more diastereomers thereof;
or a mixture of enantiomers thereof;
or an individual enantiomer or diastereoisomer thereof;
or a pharmaceutically acceptable salt of any one of the foregoing.

In embodiment (D2), there is provided the method of embodiment (D1), wherein the FPR receptor is selected from a group of FPR receptor subtypes consisting of:
(i) FPR1;
(ii) FPR1 and FPR2;
(iii) FPR1 and FPR3; and
(iv) FPR1, FPR2 and FPR3.

In embodiment (D3), there is provided the method of embodiment (D1) or (D2), wherein the compound serves as a control.

In embodiment (D4), there is provided the method of any one of embodiments (D1) through (D3), wherein the method identifies the substance as an FPR modulator.

In embodiment (D5), there is provided the method of any one of embodiments (D1) through (D4), wherein the determining of the ability of the test substance to modulate the FPR receptor comprises determining an increase or decrease in the FPR receptor activity level.

In embodiment (D6), there is provided the method of embodiment (D5), wherein the increase or decrease in the FPR receptor activity level indicates that the substance is an FPR receptor agonist or antagonist, respectively.

In embodiment (D7), there is provided the method of any one of embodiments (D1) through (D6), wherein the method indicates that the substance is a selective FPR1 receptor subtype agonist.

In embodiment (D8), there is provided the method of any one of embodiments (D1) through (D6), wherein the method indicates that the substance is an FPR1 receptor subtype agonist and an FPR2 receptor subtype agonist.

In embodiment (D9), there is provided the method of any one of embodiments (D1) through (D8), wherein the compound is selected from the group consisting of:

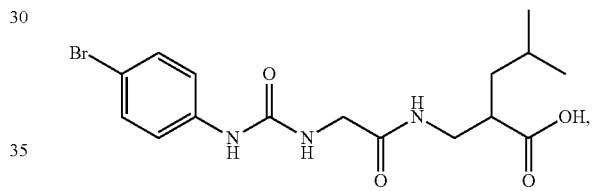

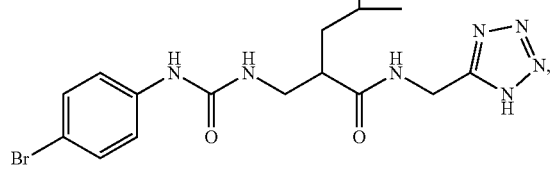

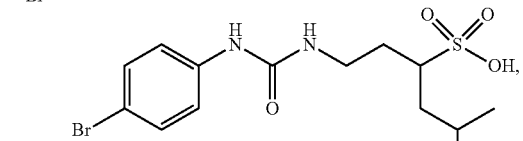

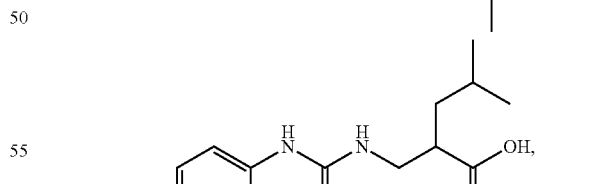

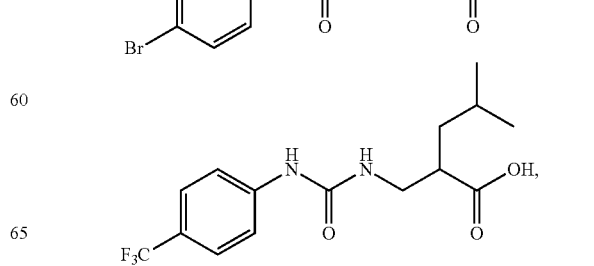

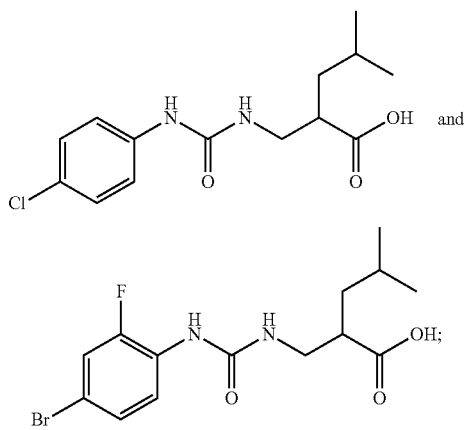

and or a mixture of two or more diastereomers thereof;
or a mixture of enantiomers thereof;
or an individual enantiomer or diastereoisomer thereof;
or a pharmaceutically acceptable salt of any of the foregoing.

In embodiment (D10), there is provided the method of embodiment (D9), wherein the compound is:

(Compound 7)

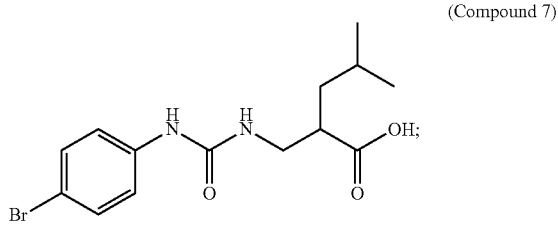 [SMILES: CC(C)CC(CNC(=O)Nc1ccc(Br)cc1)C(=O)O]

or a mixture of enantiomers thereof;
or an individual enantiomer thereof;
or a pharmaceutically acceptable salt of any one of the foregoing.

In embodiment (D11), there is provided the method of embodiment (D9), wherein the compound is:

(Compound 8)

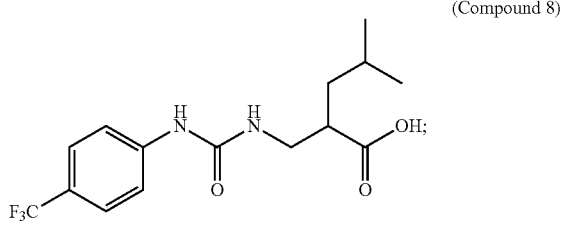 [SMILES: CC(C)CC(CNC(=O)Nc1ccc(C(F)(F)F)cc1)C(=O)O]

or a mixture of enantiomers thereof;
or an individual enantiomer thereof;
or a pharmaceutically acceptable salt of any one of the foregoing.

In embodiment (D12), there is provided the method of embodiment (D9), wherein the compound is:

(Compound 9)

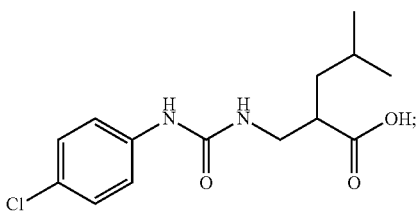

or a mixture of enantiomers thereof;
or an individual enantiomer thereof;
or a pharmaceutically acceptable salt of any one of the foregoing.

In embodiment (D13), there is provided the method of embodiment (D9), wherein the compound is:

(Compound 10)

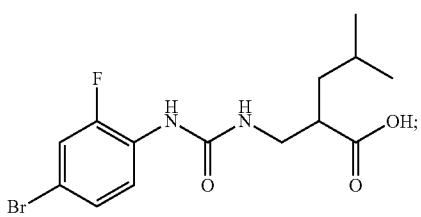

or a mixture of enantiomers thereof;
or an individual enantiomer thereof;
or a pharmaceutically acceptable salt of any one of the foregoing.

In embodiment (D14), there is provided the method of embodiment (D9), wherein the compound is:

(Compound 21)

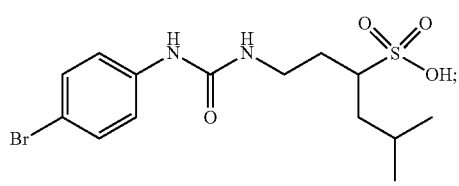

or a mixture of enantiomers thereof;
or an individual enantiomer thereof;
or a pharmaceutically acceptable salt of any one of the foregoing.

In embodiment (D15), there is provided the method of embodiment (D9), wherein the compound is:

(Compound 33)

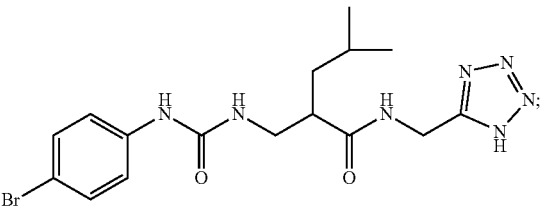

or a mixture of enantiomers thereof;
or an individual enantiomer thereof;
or a pharmaceutically acceptable salt of any one of the foregoing.

In embodiment (D16), there is provided the method of embodiment (D9), wherein the compound is:

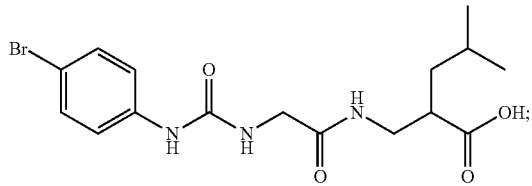
(Compound 39)

or a mixture of enantiomers thereof;
or an individual enantiomer thereof;
or a pharmaceutically acceptable salt of any one of the foregoing.

In embodiment (E1), there is provided a use of a compound of Formula I, A or II, or a pharmaceutically acceptable salt thereof, in identifying a biochemical and/or pharmacological effect(s) of agonizing an FPR1 receptor in a cell or tissue; provided that W is not —C(O)OR$_a$; preferably, the compound is selected from the group consisting of:

(a) a compound of Formula I, wherein:
W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole (preferably, W is COOH or unsubstituted tetrazole);
either n is 1, p is 0 and R$^1$ is unsubstituted C$_{1-6}$ alkyl (preferably, isobutyl), or p is 1, n is 0 and R$^2$ is unsubstituted C$_{1-6}$ alkyl (preferably, isobutyl);
R$^{2a}$ is H;
R$^3$ is H or F;
R$^4$ is H;
R$^5$ is C$_{1-6}$ haloalkyl or halogen;
R$^6$ is H;
R$^7$ is H or F;
R is H; and
k is 0;

(b) a compound of Formula A, wherein:
W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole (preferably, W is —COOH or —S(O)$_3$H);
R$^{2a}$ is H and R$^2$ is unsubstituted C$_{1-6}$ alkyl (preferably, n-propyl or isobutyl) or benzyl; or R$^{2a}$ and R$^2$ form an unsubstituted C$_{3-8}$ cycloalkyl (preferably C$_{5-8}$ or C$_{6-8}$ cycloalkyl);
R$^3$ is H or F;
R$^4$ is H;
R$^5$ is C$_{1-6}$ haloalkyl or halogen;
R$^6$ is H;
R$^7$ is H or F;
R is H; and
k is 0 or 1 (preferably, 0); and (c) a compound of Formula II, wherein
W is —COOH, sulfonate, sulfonic acid, phosphonate, phosphonic acid, phosphoric acid or Het$^1$, wherein Het$^1$ is optionally substituted tetrazole, imidazole, thiazole, oxazole, triazole, isoxazole, oxadiazole, thiadiazole, thiophene, pyrazole or pyrrole (preferably, W is —COOH or —S(O)$_3$H);
R$^2$ is unsubstituted C$_{1-6}$ alkyl (preferably, n-propyl or isobutyl) or benzyl;
R$^3$ is H or F;
R$^4$ is H;
R$^5$ is C$_{1-6}$ haloalkyl or halogen;
R$^6$ is H;
R$^7$ is H or F; and
k is 1;

or a mixture of two or more diastereomers thereof;
or a mixture of enantiomers thereof;
or an individual enantiomer or diastereoisomer thereof;
or a pharmaceutically acceptable salt of any one of the foregoing.

In embodiment (E2), there is provided a use of a compound of embodiment (E1), wherein the compound wherein the compound is selected from the group consisting of:

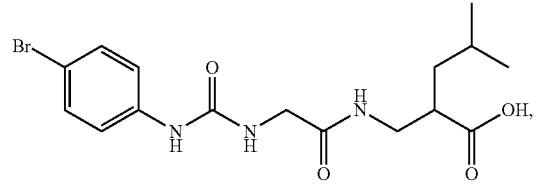

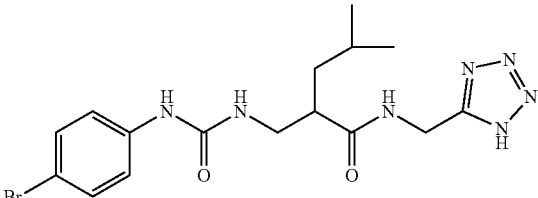

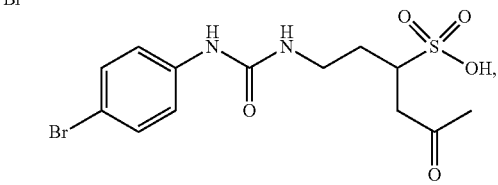

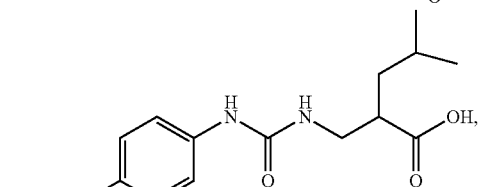

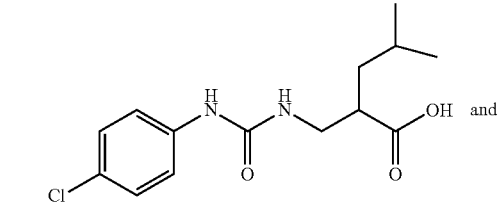
and

-continued

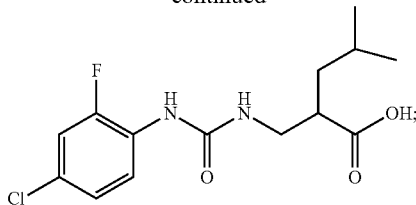

or a mixture of two or more diastereomers thereof;
or a mixture of enantiomers thereof;
or an individual enantiomer or diastereoisomer thereof;
or a pharmaceutically acceptable salt of any of the foregoing.

The present invention also concerns processes for preparing compounds of Formula I, II and/or Formula A.

Synthetic schemes and examples set forth below illustrate how the compounds according to the invention can be made, and provide details of certain specific chemical transformations. The Examples are for illustrative purposes only and are not intended, nor should they be construed, as limiting the invention in any manner. Those skilled in the art will be able to routinely modify and/or adapt the Scheme or Examples to synthesize any compound of the invention that falls within the scope of Formula I, II or A, and will appreciate that variations and modifications of the Examples can be made without exceeding the spirit or scope of the invention.

EXAMPLES

All reagents, solvents and catalysts for which the synthesis is not described are purchased from chemical vendors such as 3B Scientific, Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates were prepared according to published procedures.

Compound names were generated with ACDLab version 12.5; some intermediate and reagent names used in the Examples were generated with software such as Chem Bio Draw Ultra version 12.0, ACDLab version 12.5 or Auto Nom 2000 from MDL ISIS Draw 2.5 SP1.

In general, characterization of the compounds was performed using NMR spectroscopy. NMR spectra were acquired on a 300 or 600 MHz Varian NMR spectrometer at room temperature. Chemical shifts are given in ppm referenced either to internal TMS or to the solvent signal. Usually, the compounds of the invention were purified by medium pressure liquid chromatography, unless noted otherwise.

The following abbreviations are used herein:
Ac acetate
Boc tert-butyloxycarbonyl
$CD_3OD$ deuterated methanol
DCC N,N'-dicyclohexylcarbodiimide
DCM dichloromethane
DEA diethylamine
DIEPA diisopropylethylamine
EDCI 1-ethyl-3-(3-dimethylaminopropyl)carbodiimide
$Et_3N$ triethylamine
EtOAc ethyl acetate
$H_2$ hydrogen gas
HATU 1-[bis(dimethylamino)methylene]-1H-1,2,3-triazolo[4,5-b]pyridinium 3-oxide hexafluorophosphate
$HCO_2H$ formic acid
HOBt hydroxybenzotriazole
HPLC high performance liquid chromatography
MeOH methanol
MPLC medium pressure liquid chromatography
$Na_2SO_4$ sodium sulfate
Pd/C palladium on carbon
THE tetrahydrofuran
TMS tetramethylsilane Scheme 1. General scheme for synthesis of some compounds of the invention, including compounds of Formula II and Formula A.

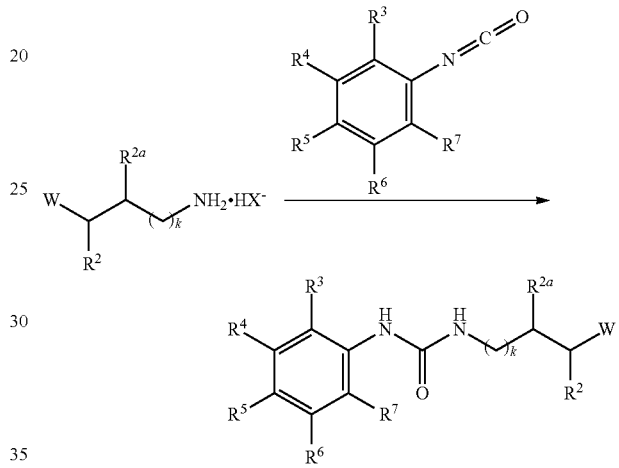

Scheme 1a. General scheme for synthesis of compounds of Formula I, wherein n is 0 and p is 1.

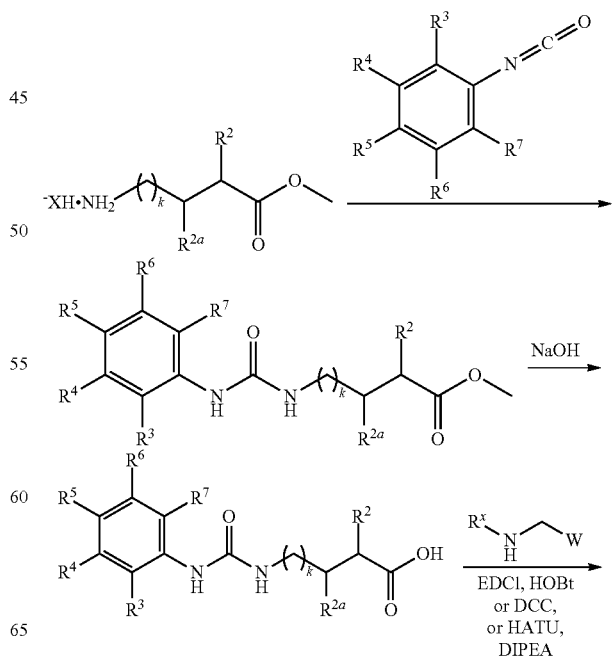

61
-continued

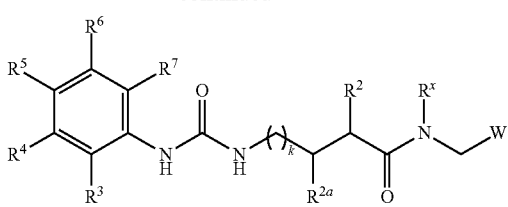

Scheme 1b. General scheme for synthesis of compounds of Formula I wherein $n$ is 1, $p$ is 0, and $R^{2a}$ is H.

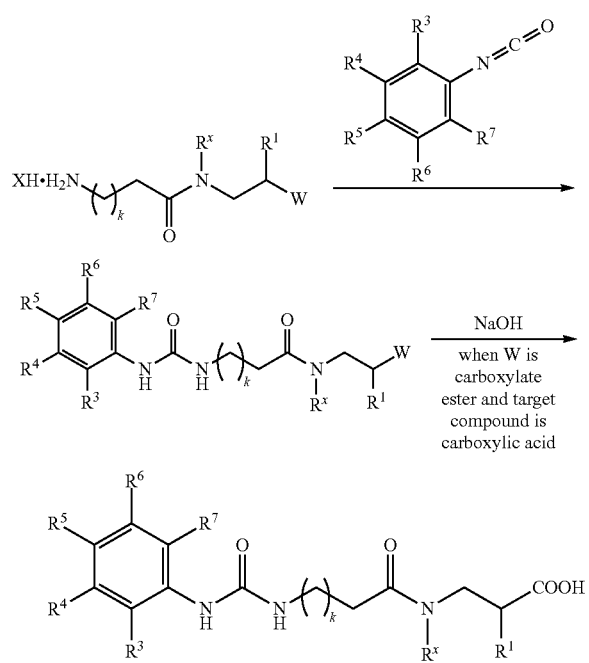

Example A—Synthesis of Intermediates

Scheme A. Synthesis of Intermediates 1 and 2.

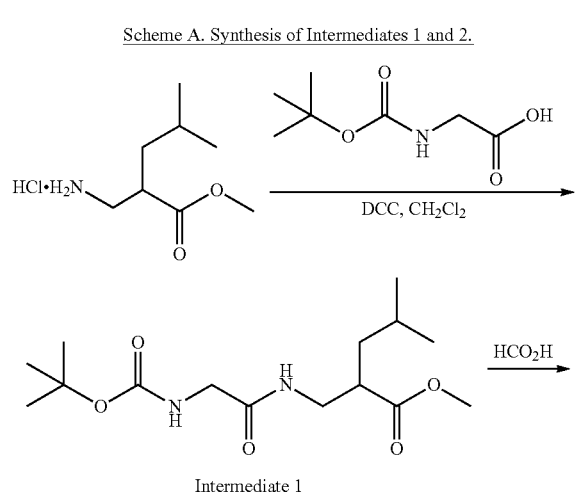

62
-continued

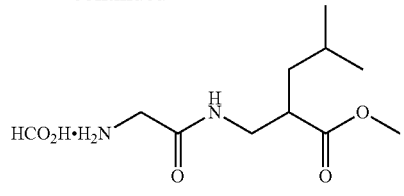

Intermediate 2

Intermediate 1. Methyl 2-((2-((tert-butoxycarbonyl)amino)acetamido)methyl)-4-methylpentanoate Intermediate 1

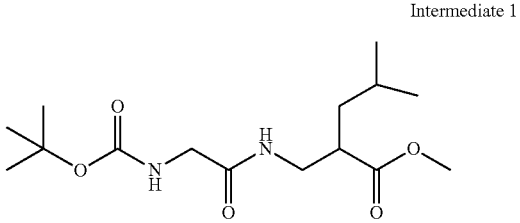 [SMILES: COC(=O)C(CNC(=O)CNC(=O)OC(C)(C)C)CC(C)C]

Intermediate 1 was prepared as outlined in Scheme A. Briefly, to a solution of methyl 2-(aminomethyl)-4-methyl pentanoate hydrochloride (300 mg, 1.53 mmol) and 20 mL of anhydrous dichloromethane at 25° C. was added DCC (316 mg, 1.53 mmol), and Boc-glycine (268 mg, 1.53 mmol). The resulting mixture was stirred at 25° C. for 12 hours. The mixture was filtered and the filtrate was concentrated under reduced pressure. The resulting product was purified by medium pressure liquid chromatography on silica gel using ethyl acetate:hexane (9:1) to yield Intermediate 1 as white solid. $^1$H NMR (CD$_3$OD, 600 MHz) δ: 3.76 (d, J=5.3 Hz, 2H), 3.69 (s, 3H), 3.48-3.54 (m, 1H), 3.32-3.39 (m, 1H), 2.69 (dd, J=7.0, 4.1 Hz, 1H), 1.59-1.63 (m, 2H), 1.45 (s, 9H), 1.36-1.38 (m, 1H), 0.91 (s, 3H), 0.90 (s, 3H).

Intermediate 2. Methyl 2-((2-aminoacetamido)methyl)-4-methylpentanoate

Intermediate 2

Intermediate 1 was prepared as outlined in Scheme A. Briefly, a solution of intermediate 1 (290 mg, 0.92 mmol) and 8 mL of formic acid was stirred at 25° C. for 4 hours. The resulting reaction was quenched with water (10 mL), and the product was extracted with EtOAc. The organic layer was washed with water, brine, dried over Na$_2$SO$_4$, filtered, and concentrated under reduced pressure to yield intermediate 7a as a white solid. $^1$H NMR (CD$_3$OD, 600 MHz) δ: 4.21 (m, 2H), 3.70 (d, J=5.3 Hz, 2H), 3.40 (s, 3H), 2.69 (m, 1H), 1.59-1.63 (m, 2H), 1.36-1.38 (m, 1H), 0.91 (s, 6H).

Example 1—Synthesis of Compounds 1 Through 6

Compound 1. Methyl 2-[({[(4-bromophenyl)amino]carbonyl}amino)methyl]-4-methylpentanoate

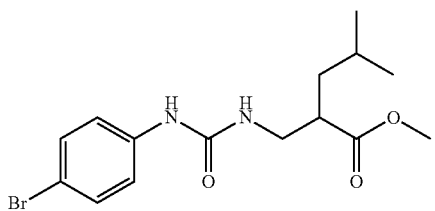

Compound 1

To a solution of methyl 2-(aminomethyl)-4-methylpentanoate hydrochloride (300 mg, 1.53 mmol) and 12 mL of methylene chloride at 25° C. was added 4-bromo-phenyl isocyanate (302 mg, 1.53 mmol) and triethylamine (0.27 mL, 1.99 mmol). The resulting mixture was stirred at 25° C. for 12 hours. The mixture was concentrated and the residue was purified by medium pressure liquid chromatography on silica gel using ethyl acetate:hexane (2:8) to yield compound 1 as white solid. $^1$H NMR (CD$_3$OD, 300 MHz) δ: 7.23-7.41 (m, 4H), 3.69 (s, 3H), 3.31-3.45 (m, 2H), 2.68-2.83 (m, 1H), 1.45-1.67 (m, 2H), 1.20-1.39 (m, 2H), 0.87-0.98 (m, 6H).

Compounds 2, 3, 4, 5 and were prepared from the corresponding beta amino acid in a similar manner to the procedure described for Compound 1. The structures and physical characteristics of compounds 2, 3, 4, 5 and 6 are described in Table 1.

TABLE 1

| Cmpd. No. | IUPAC name Structure | $^1$H NMR δ (ppm) |
|---|---|---|
| 2 | Methyl 4-methyl-2-{[({[4-(trifluoromethyl)phenyl]amino}carbonyl)amino]methyl}pentanoate | White solid; $^1$H NMR (CD$_3$OD, 300 MHz) δ: 7.52 (s, 4H), 3.69 (s, 3H), 3.32-3.48 (m, 2H), 2.67-2.83 (m, 1H), 1.50-1.68 (m, 2H), 1.25-1.41 (m, 1H), 0.93 (d, J = 4.7 Hz, 6H). |
| 3 | Methyl 2-[({[(4-chlorophenyl)amino]carbonyl}amino)methyl]-4-methylpentanoate | White solid; $^1$H NMR (CD$_3$OD, 300 MHz) δ: 7.29-7.37 (m, 2H), 7.15-7.25 (m, 2H), 3.69 (s, 3H), 3.37 (m, 2H), 2.69-2.82 (m, 1H), 1.48-1.68 (m, 2H), 1.26-1.39 (m, 1H), 0.92 (dd, J = 6.2, 1.5 Hz, 6H). |
| 4 | Methyl 2[({[(4-bromo-2-fluorophenyl)amino]carbonyl}amino)methyl]-4-methylpentanoate | White solid; $^1$H NMR (CD$_3$OD, 300 MHz) δ: 7.95 (t, J = 8.6 Hz, 1H), 7.27-7.33 (m, 1H), 7.23 (d, J = 8.8 Hz, 1H), 3.37-3.46 (m, 1H), 3.32-3.34 (m, 1H), 2.68-2.80 (m, 1H), 1.49-1.66 (m, 2H), 1.25-1.39 (m, 1H), 0.92 (dd, J = 6.3, 1.9 Hz, 6H). |
| 5 | Methyl 2-[({[(4-methoxyphenyl)amino]carbonyl}amino)methyl]-4-methylpentanoate | White solid; $^1$H NMR (CD$_3$OD, 300 MHz) δ: 7.17-7.24 (m, 2H), 6.79-6.87 (m, 2H), 3.75 (s, 3H), 3.69 (s, 3H), 3.33-3.42 (m, 1H), 3.25-3.29 (m, 1H), 2.69-2.80 (m, 1H), 1.48-1.66 (m, 2H), 1.25-1.36 (m, 1H), 0.92 (dd, J = 6.4, 2.1 Hz, 6H). |

TABLE 1-continued

| Cmpd. No. | IUPAC name Structure | $^1$H NMR δ (ppm) |
|---|---|---|
| 6 | Methyl 4-methyl-2-{[({[4-(trifluoromethoxy)phenyl]amino}carbonyl)amino]methyl}pentanoate 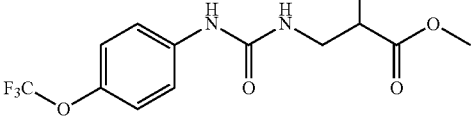 | White solid; $^1$H NMR (CD$_3$OD, 300 MHz) δ: 7.42 (d, J = 9.1 Hz, 2H), 7.15 (d, J = 8.8 Hz, 2H), 3.69 (s, 3H), 3.34-3.45 (m, 2H), 2.66-2.82 (m, 1H), 1.46-1.70 (m, 2H), 1.31 (s, 1H), 0.86-0.97 (m, 6H). |

Example 2—Synthesis of Compounds 7 Through 12

Compound 7. 2-[({[(4-Bromophenyl)amino]carbonyl}amino)methyl]-4-methylpentanoic acid Compound 7

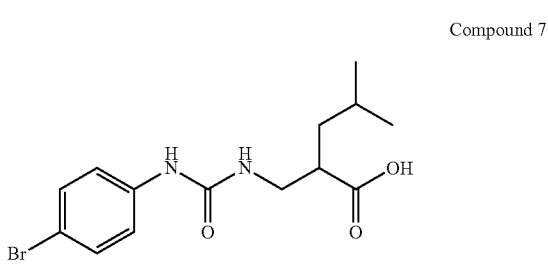 [SMILES: CC(C)CC(CNC(=O)Nc1ccc(Br)cc1)C(=O)O]

A solution of compound 1 (1.23 g, 3.44 mmol), 6N NaOH (3.44 mL, 20.6 mmol) and 15 mL of MeOH was stirred at 50° C. for 12 hours. The resulting mixture was quenched with 10% HCl (15 mL) to pH 2, then extracted with ethyl acetate. The organic layer was washed with water, brine, dried over Na$_2$SO$_4$, filtered, and the filtrate was concentrated under reduced pressure. The residue was rinsed four times with acetone:hexane (2:98) to yield compound 7 as a white solid. $^1$H NMR (CD$_3$OD, 300 MHz) δ: 7.24-7.40 (m, 4H), 3.34-3.47 (m, 1H), 3.26 (m, 1H), 2.68 (tt, J=8.5, 5.6 Hz, 1H), 1.48-1.74 (m, 2H), 1.25-1.39 (m, 1H), 0.94 (dd, J=6.4, 0.9 Hz, 6H).

Compounds 8, 9, 10, 11 and 12 were prepared from the corresponding urea derivative in a similar manner to the procedure described for compound 7. The structures and physical characteristics of compounds 8, 9, 10, 11 and 12 are described in Table 2.

TABLE 2

| Cmpd. No. | IUPAC name Structure | $^1$H NMR δ (ppm) |
|---|---|---|
| 8 | 4-Methyl-2-{[({[4-(trifluoromethyl)phenyl]amino}carbonyl)amino]methyl}pentanoic acid 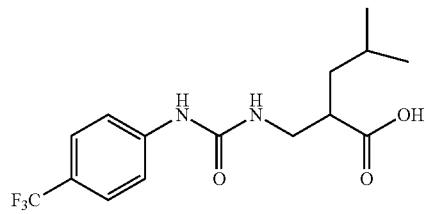 [SMILES: CC(C)CC(CNC(=O)Nc1ccc(C(F)(F)F)cc1)C(=O)O] | White solid; $^1$H NMR (CD$_3$OD, 300 MHz) δ: 7.52 (s, 4H), 3.32-3.48 (m, 2H), 2.63-2.78 (m, 1H), 1.49-1.76 (m, 2H), 1.26-1.39 (m, 1H), 0.95 (d, J = 6.2 Hz, 6H). |
| 9 | 2-[({[(4-Chlorophenyl)amino]carbonyl}amino)methyl]-4-methylpentanoic acid 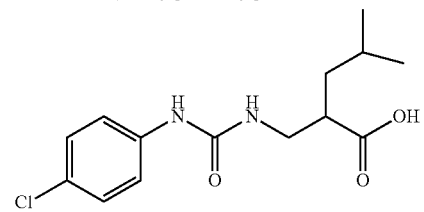 [SMILES: CC(C)CC(CNC(=O)Nc1ccc(Cl)cc1)C(=O)O] | White solid, $^1$H NMR (CD$_3$OD, 300 MHz) δ: 7.31-7.38 (m, 2H), 7.18-7.25 (m, 2H), 3.35-3.47 (m, 1H), 3.17-3.29 (m, 1H), 2.60-2.76 (m, 1H), 1.49-1.74 (m, 2H), 1.23-1.39 (m, 1H), 0.87-0.98 (m, 6H). |

TABLE 2-continued

| Cmpd. No. | IUPAC name Structure | $^1$H NMR δ (ppm) |
|---|---|---|
| 10 | 2-[({[(4-Bromo-2-fluorophenyl)amino]carbonyl}amino)methyl]-4-methylpentanoic acid 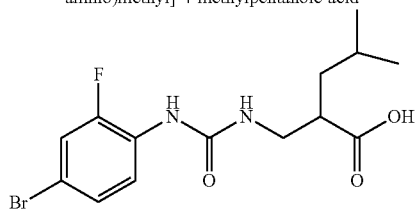 | White solid, $^1$H NMR (CD$_3$OD, 300 MHz) δ: 7.89-8.03 (m, 1H), 7.29 (d, J = 10.5 Hz, 1H), 7.20-7.25 (m, 1H), 3.35-3.46 (m, 1H), 3.18-3.29 (m, 1H), 2.68 (m, 1H), 1.49-1.74 (m, 2H), 1.25-1.39 (m, 1H), 0.94 (d, J = 6.4 Hz, 6H). |
| 11 | 2-[({[(4-methoxyphenyl)amino]carbonyl}amino)methyl]-4-methylpentanoic acid 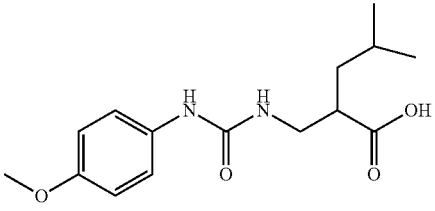 [SMILES: COc1ccc(NC(=O)NCC(CC(C)C)C(=O)O)cc1] | White solid, $^1$H NMR (CD$_3$OD, 300 MHz) δ: 7.21 (d, J = 9.1 Hz, 2H), 6.83 (d, J = 9.1 Hz, 2H), 3.75 (s, 3H), 3.34-3.44 (m, 1H), 3.25 (m, 1H), 2.62-2.76 (m, 1H), 1.61-1.76 (m, 1H), 1.47-1.60 (m, 1H), 1.23-1.37 (m, 1H), 0.94 (d, J = 6.4 Hz, 6H). |
| 12 | 4-Methyl-2-{[({[4-(trifluoromethoxy)phenyl]amino}carbonyl)amino]methyl}pentanoic acid 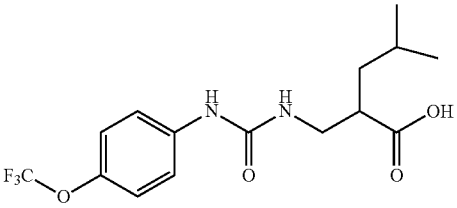 [SMILES: CC(C)CC(CNC(=O)Nc1ccc(OC(F)(F)F)cc1)C(=O)O] | White solid, $^1$H NMR (CD$_3$OD, 300 MHz) δ: 7.42 (d, J = 8.8 Hz, 2H), 7.14 (d, J = 8.2 Hz, 2H), 3.35-3.48 (m, 1H), 3.30 (m, 3H), 2.62-2.77 (m, 1H), 1.61-1.77 (m, 1H), 1.47-1.60 (m, 1H), 1.32 (ddd, J = 13.5, 7.8, 6.0 Hz, 1H), 0.94 (d, J = 6.7 Hz, 6H). |

Example 3—Synthesis of Compounds 13 Through 20

Compound 13. 2-((3-(4-Bromophenyl)ureido)methyl)-3-methylbutanoic acid

Compound 13

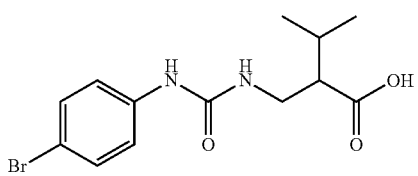 [SMILES: CC(C)C(CNC(=O)Nc1ccc(Br)cc1)C(=O)O]

To a solution of 2-(aminomethyl)-3-methylbutanoic acid hydrochloride (200 mg, 1.19 mmol) and 14 mL of methylene chloride at 25° C. was added 4-bromo-phenyl isocyanate (236 mg, 1.19 mmol) and triethylamine (0.25 mL, 1.78 mmol). The resulting mixture was stirred at 25° C. for 12 hours. The mixture was concentrated and the residue was purified by medium pressure liquid chromatography on silica gel using methanol:dichloromethane (1:9) to yield compound 13 as white solid. $^1$H NMR (CD$_3$OD, 300 MHz) δ: 7.23-7.45 (m, 4H), 3.52 (dd, J=13.6, 4.2 Hz, 1H), 3.31-3.35 (m, 1H), 2.33-2.54 (m, 1H), 1.91-2.10 (m, 1H), 0.95-1.10 (m, 6H).

Compounds 14, 15, 16, 17, 18, 19 and 20 were prepared from the corresponding beta amino acid in a similar manner to the procedure described for compound 13. The structures and physical characteristics of compounds 14, 15, 16, 17, 18, 19 and 20 are described in Table 3.

TABLE 3

| Cmpd. No. | IUPAC name Structure | $^1$H NMR δ (ppm) |
|---|---|---|
| 14 | 2-((3-(4-Bromophenyl)ureido)methyl)pentanoic acid | White solid; $^1$H NMR (CD$_3$OD, 300 MHz) δ: 7.24-7.45 (m, 4H), 3.32-3.49 (m, 2H), 2.53-2.67 (m, 1H), 1.55-1.70 (m, 1H), 1.45-1.54 (m, 1H), 1.33-1.45 (m, 2H), 0.88-1.02 (m, 3H). |
| 15 | 2-Benzyl-3-(3-(4-bromophenyl)ureido)propanoic acid | White solid; $^1$H NMR (CD$_3$OD, 300 MHz) δ: 7.14-7.39 (m, 9H), 3.32-3.49 (m, 2H), 2.80-3.02 (m, 3H). |
| 16 | 3-(3-(4-Bromophenyl)ureido)-2-methylpropanoic acid | White solid; $^1$H NMR (CD$_3$OD, 300 MHz) δ: 7.22-7.44 (m, 4H), 3.35 (d, J = 6.4 Hz, 2H), 2.66 (dq, J = 13.7, 6.9 Hz, 1H), 1.18 (d, J = 7.3 Hz, 3H). |
| 17 | 2-((3-(4-Bromophenyl)ureido)methyl)butanoic acid | White solid; $^1$H NMR (CD$_3$OD, 300 MHz) δ: 7.23-7.43 (m, 4H), 3.32-3.49 (m, 2H), 2.46-2.60 (m, 1H), 1.50-1.74 (m, 2H), 0.92-1.05 (m, 3H). |
| 18 | (1R*,2R*)-2-(3-(4-Bromophenyl)ureido)cyclohexane carboxylic acid (racemic mixture) | White solid; [α]D = 0, c = 1.00, DMF, $^1$H NMR (CD$_3$OD, 600 MHz) δ: 7.32-7.36 (m, 2H), 7.25-7.29 (m, 2H), 3.81 (td, J = 11.0, 3.8 Hz, 1H), 2.27 (td, J = 11.2, 3.5 Hz, 1H), 2.01-2.06 (m, 1H), 1.95-2.00 (m, 1H), 1.71-1.79 (m, 2H), 1.58 (qd, J = 12.7, 3.5 Hz, 1H), 1.37-1.46 (m, 1H), 1.22-1.32 (m, 2H). |

TABLE 3-continued

| Cmpd. No. | IUPAC name Structure | $^1$H NMR δ (ppm) |
|---|---|---|
| 19 | (1R*,2S*)-2-(3-(4-Bromophenyl)ureido)cyclohexane carboxylic acid<br><br>(racemic mixture) | White solid; [α]D = 0, c = 1.00, DMF, $^1$H NMR (CD$_3$OD, 600 MHz) δ: 7.32-7.36 (m, 2H), 7.23-7.30 (m 2H), 3.81 (td, J = 10.9, 4.1 Hz, 1H), 2.28 (td, J = 11.2, 3.5 Hz, 1H), 1.96-2.06 (m, 2H), 1.72-1.80 (m, 2H), 1.54-1.63 (m, 1H), 1.36-1.48 (m, 1H), 1.23-1.33 (m, 2H). |
| 20 | 2-(3-(4-Bromophenyl)ureido)cyclooctane carboxylic acid | White solid; $^1$H NMR (CD$_3$OD, 600 MHz) δ: 7.32-7.39 (m, 2H), 7.25-7.30 (m, 2H), 4.34 (dt, J = 10.4, 3.9 Hz, 1H), 2.86 (dt, J = 10.0, 4.1 Hz, 1H), 1.96-2.02 (m, 1H), 1.83-1.94 (m, 2H), 1.74-1.81 (m, 2H), 1.58-1.71 (m, 7H). |

Example 4—Synthesis of Compound 21

Compound 21. 1-(3-(4-Bromophenyl)ureido)-5-methylhexane-3-sulfonic acid

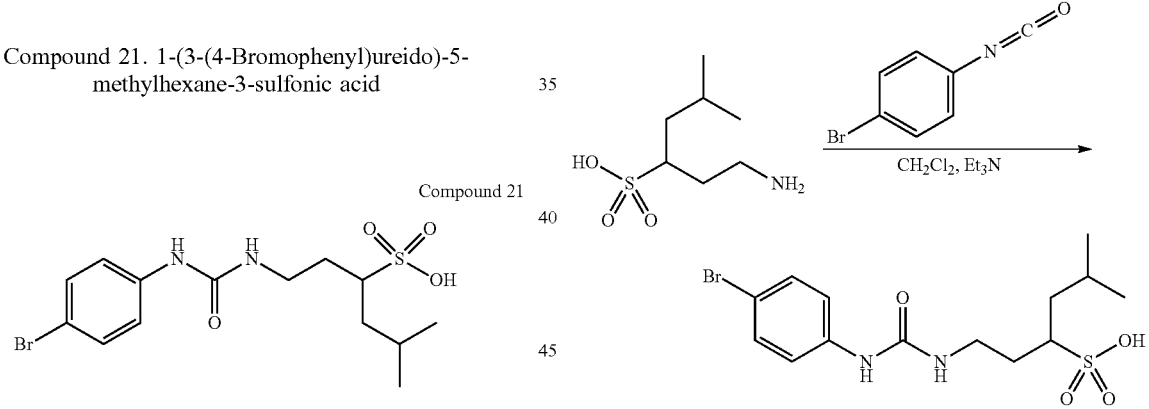

To a solution of 1-amino-5-methylhexane 3-sulfonic acid (150 mg, 0.77 mmol) and 8 mL of methylene chloride at 25° C. was added 4-bromo-phenyl isocyanate (152 mg, 0.77 mmol) and triethylamine (0.16 mL, 1.15 mmol). The resulting mixture was stirred at 25° C. for 12 hours. The mixture was quenched with 10% HCl (1 mL) to pH 2 then extracted with ethyl acetate. The organic layer was washed with water, brine, dried over Na$_2$SO$_4$, filtered, and the filtrate was concentrated under reduced pressure. The residue was purified by medium pressure liquid chromatography on silica gel using methanol:dichloromethane (15:85) to yield compound 21 as white solid. $^1$H NMR (CD$_3$OD, 600 MHz) δ: 7.24-7.43 (m, 4H), 3.41 (s, 2H), 2.79 (dd, J=7.3, 4.4 Hz, 1H), 1.95-2.05 (m, 1H), 1.77-1.93 (m, 3H), 1.43 (t, J=8.5 Hz, 1H), 0.94 (d, J=6.5 Hz, 3H), 0.90 (d, J=5.9 Hz, 3H).

Example 5—Synthesis of Compounds 31 Through 39

Compound 31. t-Butyl ({2-[({[(4 bromophenyl)amino]carbonyl}amino)methyl]-4-methylpentanoyl}amino)acetate Compound 31

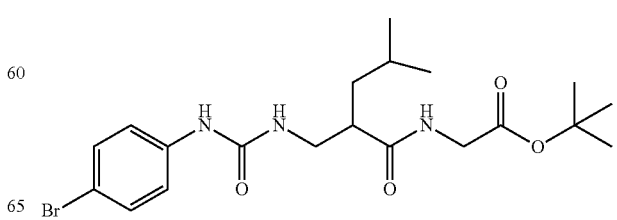

To a solution of compound 1 (168 mg, 0.49 mmol) and 20 mL of anhydrous dichloromethane at 25° C. was added DCC (101 mg, 0.49 mmol), and glycine tert-butyl ester (71 mg, 0.87 mmol). The resulting mixture was stirred at 25° C. for 12 hours. The mixture was filtered and filtrate was concentrated under reduced pressure. The resulting product was purified by medium pressure liquid chromatography on silica gel using ethyl acetate:hexane (3:7) to yield compound 31 as white solid. $^1$H NMR (CD$_3$OD, 300 MHz) δ: 7.23-7.42 (m, 4H), 3.79-3.87 (m, 2H), 3.34-3.48 (m, 1H), 3.13-3.25 (m, 1H), 2.58-2.75 (m, 1H), 1.58-1.80 (m, 2H), 1.46 (s, 9H), 1.24-1.39 (m, 1H), 0.93 (t, J=5.7 Hz, 6H).

Compounds 32 and 34 were prepared from the corresponding carboxylic acid derivative in a similar manner to the procedure described for compound 31. Their characteristics are described in Table 4.

at 25° C. was added DCC (48 mg, 0.23 mmol), and (1H-tetrazol-5-ylmethyl)amine hydrochloride (25 mg, 0.25 mmol). The resulting mixture was stirred at 25° C. for 12 hours. The mixture was filtered and filtrate was concentrated under reduced pressure.

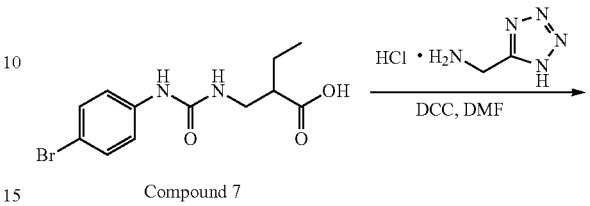

Compound 7

TABLE 4

| Cmpd. No. | IUPAC name Structure | $^1$H NMR δ (ppm) |
|---|---|---|
| 32 | tert-Butyl 2-(2-((3-(4-bromophenyl)ureido)methyl)-N,4-dimethylpentanamido)acetate 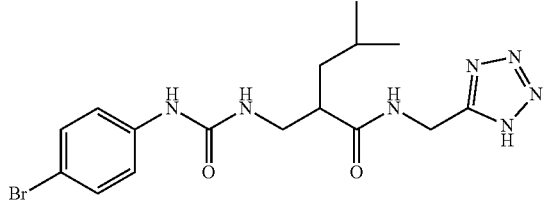 | White solid; $^1$H NMR (CD$_3$OD, 300 MHz) δ: 7.24-7.42 (m, 4H), 3.90-4.21 (m, 2H), 3.32-3.41 (m, 1H), 3.22-3.27 (m, 1H), 3.17 (s, 3H), 1.51-1.71 (m, 2H), 1.46 (s, 9H), 1.20-1.37 (m, 2H), 0.91-1.00 (m, 6H). |
| 34 | 2-((3-(4-bromophenyl)ureido)methyl)-N,N,4-trimethylpentanamide 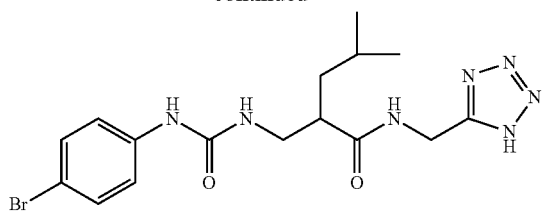 | White solid; $^1$H NMR (CD$_3$OD, 300 MHz) δ: 7.23-7.42 (m, 4H), 3.32-3.38 (m, 1H), 3.20-3.26 (m, 1H), 3.13 (s, 3H), 2.96 (s, 3H), 1.47-1.66 (m, 2H), 1.23-1.36 (m, 1H), 0.92 (dd, J = 6.3, 3.1 Hz, 6H). |

Compound 33

N-((1H-tetrazol-5-yl)methyl)-2-((3-(4-bromophenyl)ureido)methyl)-4-methylpentanamide Compound 33

To a solution of 2-[({[(4-Bromophenyl)amino]carbonyl}amino)methyl]-4-methylpentanoic acid (compound 7; 80 mg, 0.23 mmol) and 2 mL of anhydrous DMF -continued Compound 33

The resulting product was purified by medium pressure liquid chromatography on silica gel using methanol:dichloromethane (15:85) to yield compound 33 as white solid. $^1$H NMR (CD$_3$OD, 300 MHz) δ: 7.25-7.41 (m, 4H), 4.78-4.87 (m, 8H), 4.51 (d, J=15.8 Hz, 1H), 3.48 (dd, J=13.3, 4.5 Hz, 1H), 3.18 (dd, J=13.6, 9.2 Hz, 1H), 2.63 (br. s., 1H), 1.50-1.69 (m, 2H), 1.18-1.31 (m, 1H), 0.92 (dd, J=6.2, 3.8 Hz, 6H).

75

Compound 35. 2-((3-(4-bromophenyl)ureido)methyl)-4-methylpentanamide

Compound 35

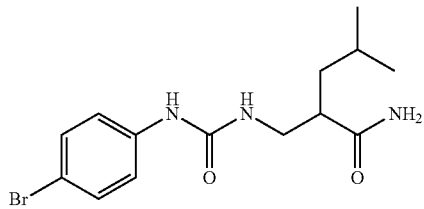 [SMILES: CC(C)CC(CNC(=O)Nc1ccc(Br)cc1)C(N)=O]

To a solution of compound 7 (100 mg, 0.29 mmol) and 5 mL of anhydrous tetrahydrofuran under argon at −78° C. was added triethylamine (39 mg, 0.38 mmol), and ethyl chloroformate (38 mg, 0.37 mmol). The mixture was stirred at −78° C. for 30 minutes, then ammonia gas was bubbled into reaction flask for 1 minutes. The resulting mixture was stirred at 25° C. for 1 hour.

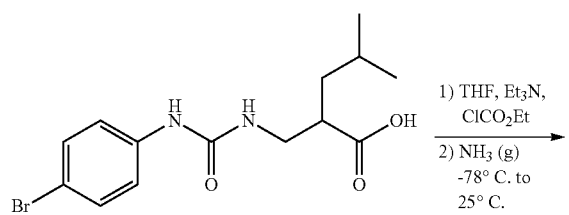

Compound 7

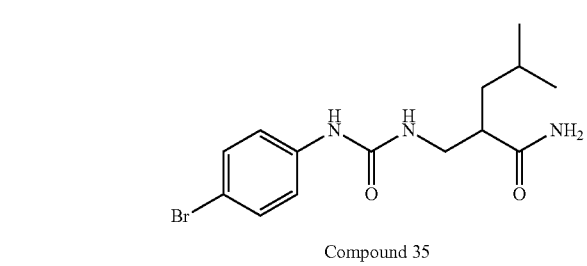

Compound 35

The mixture was quenched with water (1 mL) then extracted with ethyl acetate (20 mL). The layers were separated, and the organic layer was washed with water, brine, dried over $Na_2SO_4$, filtered, and concentrated under reduced pressure. The resulting product was purified by preparative thin layer chromatography on silica gel using an eluent of 100% ethyl acetate to yield compound 35 as a white solid. $^1$H NMR ($CD_3OD$, 300 MHz) δ: 7.26-7.42 (m, 4H), 3.32-3.40 (m, 1H), 3.14-3.27 (m, 1H), 2.59-2.75 (m, 1H), 1.47-1.69 (m, 2H), 1.17-1.30 (m, 1H), 0.94 (dd, J=6.4, 1.8 Hz, 6H).

76

Compound 36. ({2-[({[(4-bromophenyl)amino]carbonyl}amino)methyl]-4-methylpentanoyl}amino)acetic acid Compound 36

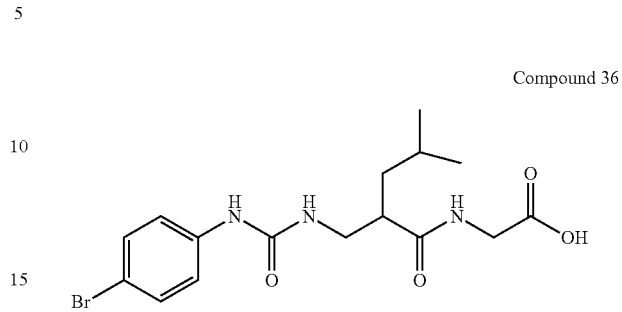

A solution of compound 31 (181 mg, 0.40 mmol) and 8 mL of formic acid was stirred at 25° C. for 12 hours. The resulting reaction was quenched with water (10 mL), and the product was extracted with EtOAc. The organic layer was washed with water, brine, dried over $Na_2SO_4$, filtered, and concentrated under reduced pressure. The residue was rinsed four times with acetone:hexane (2:98) to yield compound 36 as a white solid. $^1$H NMR ($CD_3OD$, 300 MHz) δ: 7.22-7.42 (m, 4H), 3.81-4.04 (m, 2H), 3.37-3.53 (m, 1H), 3.10-3.24 (m, 1H), 2.54-2.76 (m, 1H), 1.77-1.91 (m, 2H), 1.14-1.32 (m, 1H), 0.93 (t, J=5.7 Hz, 6H).

Compound 37

2-(2-((3-(4-bromophenyl)ureido)methyl)-N,4-dimethylpentanamido)acetic acid

Compound 37

Compound 37 was prepared from the corresponding ester derivative in a similar manner to the procedure described for compound 36. It was obtained as a white solid; $^1$H NMR ($CD_3OD$, 300 MHz) δ: 7.25-7.41 (m, 4H), 4.03-4.23 (m, 2H), 3.33-3.46 (m, 1H), 3.25-3.29 (m, 1H), 3.17 (s, 3H), 1.49-1.73 (m, 2H), 1.22-1.37 (m, 2H), 0.90-1.05 (m, 6H).

Example 6—Synthesis of Compounds 38 and 39

Compounds 38 and 39 were prepared as generally outlined in Scheme 1b.

Compound 38. Methyl 2-((2-(3-(4-bromophenyl)ureido)acetamidomethyl-4-methylpentanoate

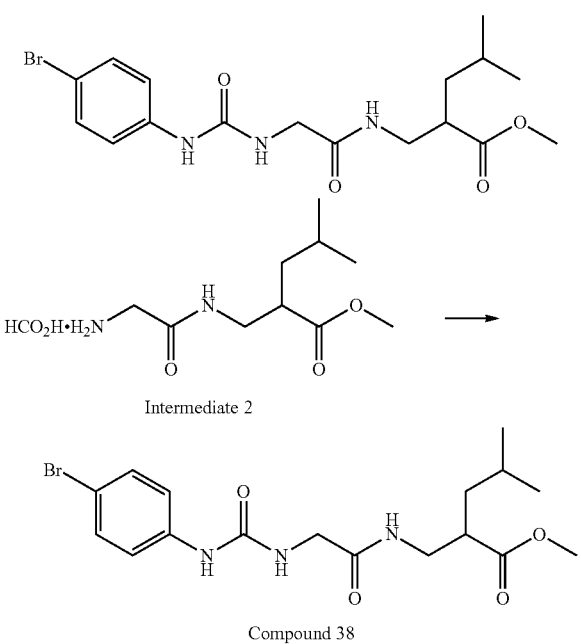

Compound 38

Intermediate 2

Compound 38

To a solution of methyl 2-((2-aminoacetamido)methyl)-4-methylpentanoate (intermediate 2; 81 mg, 0.38 mmol) and 12 mL of methylene chloride at 25° C. was added 4-bromophenyl isocyanate (74 mg, 0.38 mmol) and triethylamine (0.08 mL, 0.57 mmol). The resulting mixture was stirred at 25° C. for 12 hours. The mixture was concentrated and the residue was purified by medium pressure liquid chromatography on silica gel using ethyl acetate:hexane (9:1) to yield compound 38 as white solid. $^1$H NMR (CD$_3$OD, 600 MHz) δ: 7.35 (s, 2H), 7.30-7.33 (m, 2H), 3.77-3.85 (m, 2H), 3.65 (s, 3H), 3.34-3.37 (m, 2H), 2.70-2.76 (m, 1H), 1.50-1.59 (m, 2H), 1.26-1.31 (m, 1H), 0.89 (dd, J=6.5, 1.8 Hz, 6H).

Compound 39. 2-((2-(3-(4-Bromophenyl)ureido)acetamido)methyl)-4-methylpentanoic acid

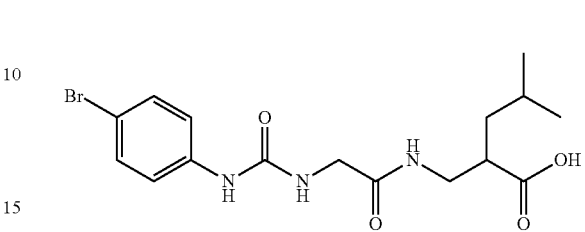

Compound 39 was prepared from compound 38 using similar conditions to those described for compound 7. Compound 39 was obtained as a white solid, $^1$H NMR (CD$_3$OD, 600 MHz) δ: 7.55-7.58 (m, 2H), 7.51-7.54 (m, 2H), 4.00-4.07 (m, 2H), 3.56-3.61 (m, 1H), 3.47 (m, 1H), 2.75 (br. s., 1H), 1.85 (dt, J=13.1, 6.7 Hz, 1H), 1.72-1.77 (m, 1H), 1.42 (dt, J=13.5, 6.7 Hz, 1H), 1.11 (t, J=6.7 Hz, 6H).

Biological Data

Biological activity of some specific compounds of the invention is set forth in Table 5 and Table 6 below. CHO-Gα16 cells stably expressing FPR1 or FPR2 were cultured in: Ham's F12 nutrient media, 10% fetal bovine serum, 1% PSA (penicillin, streptomycin, amphotericin B antiobiotic/antimycotic), 400 µg/ml geneticin and 50 µg/ml hygromycin. In general, the day before the experiment, 18,000 cells/well were plated in a 384-well clear bottom poly-D-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 5

| Compound Number | Structure | FPR2 Gα16-CHO EC$_{50}$ (% eff) | FPR1 Gα16-CHO EC$_{50}$ (% eff) | Ratio FPR2:FPR1 (EC$_{50}$) |
|---|---|---|---|---|
| 1 | 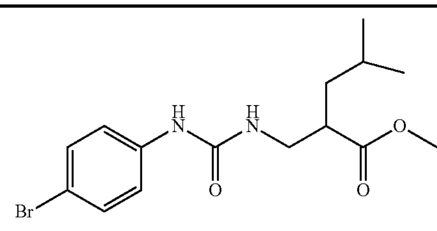 | 678 nM (0.47) | 4030 nM (0.72) | 0.17 |
| 2 | 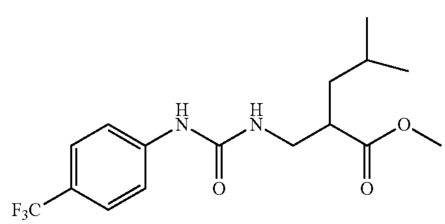 | 2204 nM (0.78) | 10449 nM (0.57) | 0.21 |

TABLE 5-continued

| Compound Number | Structure | FPR2 Gα16-CHO EC$_{50}$ (% eff) | FPR1 Gα16-CHO EC$_{50}$ (% eff) | Ratio FPR2:FPR1 (EC$_{50}$) |
|---|---|---|---|---|
| 3 | 4-Cl-phenyl urea, methyl ester of 2-(aminomethyl)-4-methylpentanoate | 1322 nM (0.95) | >10K nM (0.50) | <1 |
| 4 | 4-Br-2-F-phenyl urea, methyl ester | 1527 nM (0.98) | >19K nM (0.21) | <1 |
| 5 | 4-MeO-phenyl urea, methyl ester | 541 nM (0.42) | >73K nM (0.65) | <1 |
| 6 | 4-F$_3$CO-phenyl urea, methyl ester | >1K (0.67) | >15K nM (0.39) | ND |
| 7 | 4-Br-phenyl urea, carboxylic acid | 1297 nM (0.90) | 35 nM (0.97) | 37 |
| 8 | 4-F$_3$C-phenyl urea, carboxylic acid | 1350 nM (0.92) | 54 nM (1.05) | 25 |
| 9 | 4-Cl-phenyl urea, carboxylic acid | 3004 nM (81) | 163 nM (0.95) | 18 |

TABLE 5-continued

| Compound Number | Structure | FPR2 Gα16-CHO EC$_{50}$ (% eff) | FPR1 Gα16-CHO EC$_{50}$ (% eff) | Ratio FPR2:FPR1 (EC$_{50}$) |
| --- | --- | --- | --- | --- |
| 10 | 4-bromo-2-fluorophenyl urea isobutyl carboxylic acid | 1911 nM (0.94) | 113 nM (0.98) | 17 |
| 11 | 4-methoxyphenyl urea isobutyl carboxylic acid | >1K (0.56) | 1216 nM (0.92) | Not determined |
| 12 | 4-trifluoromethoxyphenyl urea isobutyl carboxylic acid | 8085 nM (0.40) | 1176 nM (0.81) | 6.9 |
| 13 | 4-bromophenyl urea isopropyl carboxylic acid | 2669 nM (0.83) | 2188 nM (0.97) | 1.2 |
| 14 | 4-bromophenyl urea propyl carboxylic acid | 1324 nM (0.83) | 243 nM (0.99) | 5.4 |
| 15 | 4-bromophenyl urea benzyl carboxylic acid | 351 nM (0.93) | 67 nM (0.94) | 5.2 |
| 16 | 4-bromophenyl urea methyl carboxylic acid | 3073 nM (0.62) | 2846 nM (0.84) | 1.1 |

TABLE 5-continued

| Compound Number | Structure | FPR2 Ga16-CHO EC$_{50}$ (% eff) | FPR1 Ga16-CHO EC$_{50}$ (% eff) | Ratio FPR2:FPR1 (EC$_{50}$) |
|---|---|---|---|---|
| 17 | [structure: 4-bromophenyl urea with CH$_2$-CH(Et)-COOH] | 2271 nM (0.71) | 2150 nM (0.85) | 1.1 |
| 18 | [structure: trans-2-(3-(4-bromophenyl)ureido)cyclohexane-1-carboxylic acid] (racemic mixture) | 246 nM (0.98) | 47 nM (1.01) | 5.2 |
| 19 | [structure: cis-2-(3-(4-bromophenyl)ureido)cyclohexane-1-carboxylic acid] (racemic mixture) | 48 nM (1.02) | 14 nM (0.97) | 3.4 |
| 20 | [structure: 2-(3-(4-bromophenyl)ureido)cyclooctane-1-carboxylic acid] | 82 nM (0.97) | 51 nM (95) | 1.6 |
| 21 | [structure: 4-bromophenyl urea with sulfonic acid isobutyl chain] | 1256 nM (0.89) | 7 nM (0.99) | 179 |
| 34 | [structure: 4-bromophenyl urea with CH$_2$-CH(iBu)-C(O)N(Me)$_2$] | 314 nM (0.92) | 6320 nM (0.69) | <1 |

TABLE 5-continued

| Compound Number | Structure | FPR2 Ga16-CHO EC$_{50}$ (% eff) | FPR1 Ga16-CHO EC$_{50}$ (% eff) | Ratio FPR2:FPR1 (EC$_{50}$) |
|---|---|---|---|---|
| 35 | 4-bromophenyl-NH-C(O)-NH-CH$_2$-CH(CH$_2$CH(CH$_3$)$_2$)-C(O)-NH$_2$ | 975 nM (0.95) | 7092 nM (0.80) | 0.14 |

TABLE 6

| Compound Number | Structure | FPR2 Ga16-CHO EC$_{50}$ (% eff) | FPR1 Ga16-CHO EC$_{50}$ (% eff) | Ratio FPR2:FPR1 (EC$_{50}$) |
|---|---|---|---|---|
| 31 | 4-bromophenyl-NH-C(O)-NH-CH$_2$-CH(CH$_2$CH(CH$_3$)$_2$)-C(O)-NH-CH$_2$-C(O)-O-tBu | 1500 nM (0.18) | 552 nM (0.98) | 2.7 |
| 32 | 4-bromophenyl-NH-C(O)-NH-CH$_2$-CH(CH$_2$CH(CH$_3$)$_2$)-C(O)-N(CH$_3$)-CH$_2$-C(O)-O-tBu | 1031 nM (0.89) | 2514 nM (0.73) | 0.41 |
| 33 | 4-bromophenyl-NH-C(O)-NH-CH$_2$-CH(CH$_2$CH(CH$_3$)$_2$)-C(O)-NH-CH$_2$-tetrazole | 130 nM (0.98) | 13 nM (0.95) | 10 |
| 36 | 4-bromophenyl-NH-C(O)-NH-CH$_2$-CH(CH$_2$CH(CH$_3$)$_2$)-C(O)-NH-CH$_2$-C(O)-OH | 1000 nM (0.43) | 156 nM (0.95) | 6.4 |

TABLE 6-continued

| Compound Number | Structure | FPR2 Ga16-CHO EC$_{50}$ (% eff) | FPR1 Ga16-CHO EC$_{50}$ (% eff) | Ratio FPR2:FPR1 (EC$_{50}$) |
|---|---|---|---|---|
| 37 | 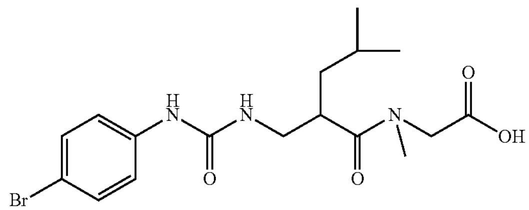 [SMILES: CC(C)CC(CNC(=O)Nc1ccc(Br)cc1)C(=O)N(C)CC(=O)O] | 12 nM (1.04) | 55 nM (0.96) | 0.22 |
| 38 | 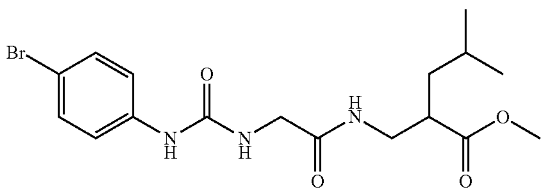 [SMILES: COC(=O)C(CNC(=O)CNC(=O)Nc1ccc(Br)cc1)CC(C)C] | 2173 nM (0.80) | 2600 nM (0.77) | 0.83 |
| 39 | 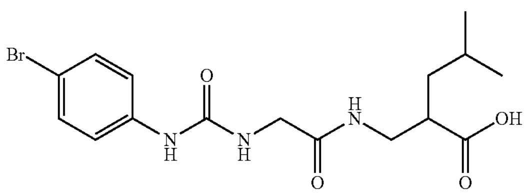 [SMILES: CC(C)CC(CNC(=O)CNC(=O)Nc1ccc(Br)cc1)C(=O)O] | 1680 nM (0.77) | 19 nM (0.96) | 88 |

What is claimed:

1. A compound of Formula I:

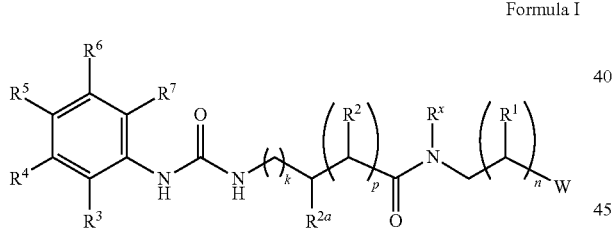

Formula I wherein:

W is —COOH, —C(O)OR$^a$, sulfonate, sulfonic acid, phosphonate, phosphonic acid, phosphoric acid, boronic acid or Het$^1$;

wherein R$^a$ is optionally substituted C$_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered heteroaryl optionally substituted with one or more halogen, unsubstituted C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$;

R$^1$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, guanido (—NHC(=NH)NH$_2$), —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;

R$^{2a}$ is H, and R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{16}$R$^{17}$, urea (—NHC(=O)NH$_2$), guanido (—NHC(=NH)NH$_2$), —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle; or R$^2$ and R$^{2a}$ form an optionally substituted C$_{3-8}$ cycloalkyl or an optionally substituted C$_{3-8}$ cycloalkenyl;

R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;

R$^4$ is H, optionally substituted C$_{1-6}$ alkyl, C$_{1-6}$ haloalkyl, halogen, —S(O)$_m$R$^{10}$ or —C(O)R$^{11}$;

R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —SR$^{13}$ or —R$^{13}$;

R$^6$ is H, optionally substituted C$_{1-6}$ alkyl, C$_{1-6}$ haloalkyl, halogen, —S(O)$_m$R$^{10}$ or —C(O)R$^{11}$;

R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;

$R^8$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^9$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^{10}$ is —OH, optionally substituted $C_{1-6}$ alkyl or optionally substituted $C_{6-10}$ aryl;

$R^{11}$ is —OH, optionally substituted $C_{1-6}$ alkyl or optionally substituted $C_{6-10}$ aryl;

$R^{12}$ is H or optionally substituted $C_{1-8}$ alkyl;

$R^{13}$ is H, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^{14}$ is $C_{1-6}$ alkyl;

$R^{15}$ is $C_{1-6}$ alkyl;

$R^{16}$ is $C_{1-6}$ alkyl;

$R^{17}$ is $C_{1-6}$ alkyl;

$R^x$ is H, optionally substituted $C_{1-6}$ alkyl, optionally substituted $C_{6-10}$ aryl or optionally substituted heterocycle;

k is 0, 1 or 2;

each m is independently 1 or 2; and either n is 0, p is 1 and $R^1$ is absent, or n is 1, p is 0 and $R^2$ is absent;

provided that when p is 0, then $R^{2a}$ is H;

or a mixture of two or more diastereomers thereof;

or a mixture of enantiomers thereof;

or an individual enantiomer or diastereoisomer thereof;

or a pharmaceutically acceptable salt of any one of the foregoing.

2. The compound of claim 1, wherein W is —COOH, sulfonate, sulfonic acid, phosphonate, phosphonic acid, phosphoric acid or $Het^1$, wherein $Het^1$ is optionally substituted tetrazole, imidazole, thiazole, oxazole, triazole, isoxazole, oxadiazole, thiadiazole, thiophene, pyrazole or pyrrole.

3. The compound of claim 1, wherein k is 0 or 1.

4. The compound of claim 1, wherein n is 0, p is 1, k is 0, and $R^{2a}$ is H, having the following structure:

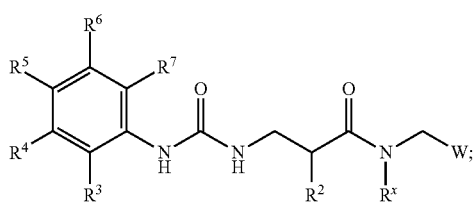

or a mixture of two or more diastereomers thereof;
or a mixture of enantiomers thereof;
or an individual enantiomer or diastereoisomer thereof;
or a pharmaceutically acceptable salt of any one of the foregoing.

5. The compound of claim 1, wherein n is 0, p is 1, k is 1, and $R^{2a}$ is H, having the following structure:

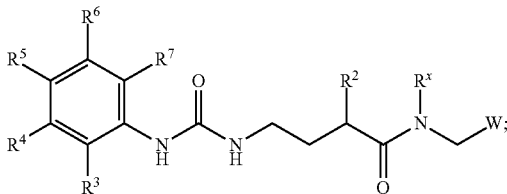

or a mixture of two or more diastereomers thereof;
or a mixture of enantiomers thereof;
or an individual enantiomer or diastereoisomer thereof;
or a pharmaceutically acceptable salt of any one of the foregoing.

6. The compound of claim 1, wherein n is 1, p is 0, k is 0, and $R^{2a}$ is H, having the following structure:

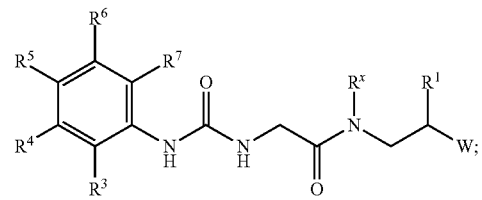

or a mixture of two or more diastereomers thereof;
or a mixture of enantiomers thereof;
or an individual enantiomer or diastereoisomer thereof;
or a pharmaceutically acceptable salt of any one of the foregoing.

7. The compound of claim 1, wherein n is 1, p is 0, k is 1, and $R^{2a}$ is H, having the following structure:

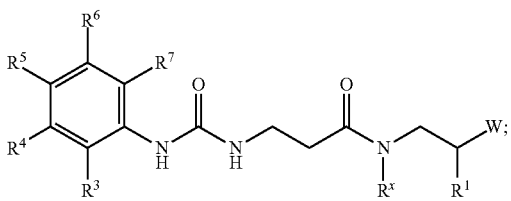

or a mixture of two or more diastereomers thereof;
or a mixture of enantiomers thereof;
or an individual enantiomer or diastereoisomer thereof;
or a pharmaceutically acceptable salt of any one of the foregoing.

8. The compound of claim 1, wherein n is 0, p is 1, k is 0, and $R^2$ and $R^{2a}$ form a hydrocarbon ring A, wherein A is optionally substituted $C_{3-8}$ cycloalkyl or optionally substituted $C_{3-8}$ cycloalkenyl, the compound having the following structure:

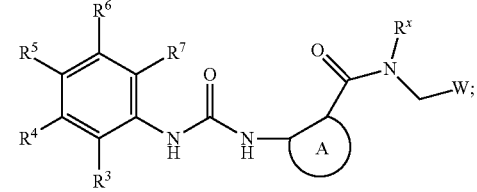

or a mixture of two or more diastereomers thereof;
or a mixture of enantiomers thereof;
or an individual enantiomer or diastereoisomer thereof;
or a pharmaceutically acceptable salt of any one of the foregoing.

9. The compound of claim 1, wherein n is 0, p is 1, k is 1, and $R^2$ and $R^{2a}$ form a hydrocarbon ring A, wherein A is optionally substituted $C_{3-8}$ cycloalkyl or optionally substituted $C_{3-8}$ cycloalkenyl, the compound having the following structure:

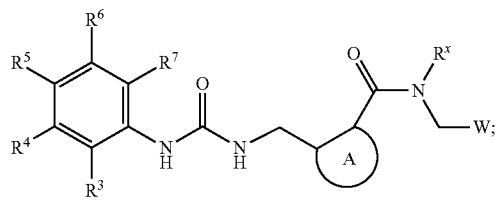

or a mixture of two or more diastereomers thereof;
or a mixture of enantiomers thereof;
or an individual enantiomer or diastereoisomer thereof;
or a pharmaceutically acceptable salt of any one of the foregoing.

10. The compound of claim 1, wherein $R^{2a}$ is H; k is 0; and either n is 1, p is 0 and $R^1$ is unsubstituted $C_{1-6}$ alkyl, or n is 0, p is 1 and $R^2$ is unsubstituted $C_{1-6}$ alkyl.

11. The compound of claim 1, wherein $R^1$ or $R^2$ is isobutyl.

12. The compound of claim 11, wherein: $R^3$ is H or F; $R^4$ is H; $R^5$ is $C_{1-6}$ haloalkyl or halogen; $R^6$ is H; and $R^7$ is H or F.

13. The compound of claim 1 selected from the group consisting of:

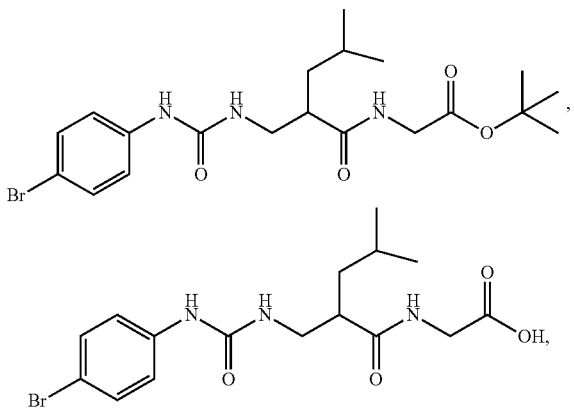

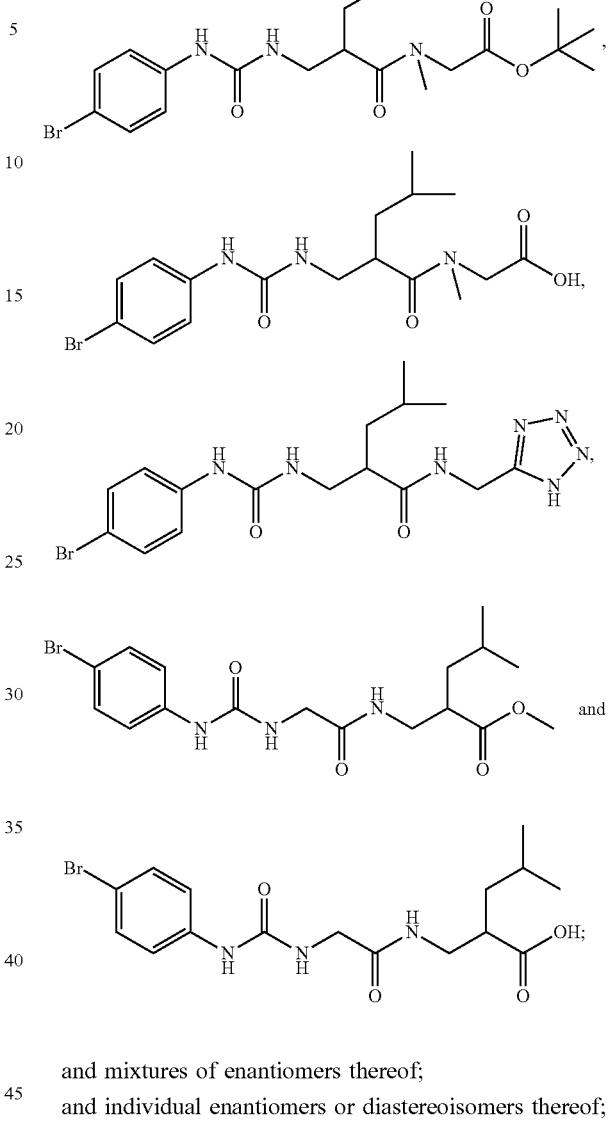

and mixtures of enantiomers thereof;
and individual enantiomers or diastereoisomers thereof;
and pharmaceutically acceptable salts thereof.

* * * * *